(12) United States Patent
Seitz et al.

(10) Patent No.: US 10,456,307 B2
(45) Date of Patent: Oct. 29, 2019

(54) ADULT DISPOSABLE ABSORBENT ARTICLES AND ARRAYS OF SAID ARTICLES COMPRISING ABSORBENT CORES HAVING CHANNELS

(71) Applicant: The Procter & Gamble Company, Cincinnati, OH (US)

(72) Inventors: Bret Darren Seitz, West Chester, OH (US); Gary Dean LaVon, Liberty Township, OH (US); Ryo Minoguchi, Cincinnati, OH (US); Alexander Fedotov, Schwalbach am Taunus (DE); Fred Naval Desai, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 815 days.

(21) Appl. No.: 14/996,683

(22) Filed: Jan. 15, 2016

(65) Prior Publication Data

US 2016/0206485 A1    Jul. 21, 2016

Related U.S. Application Data

(60) Provisional application No. 62/104,330, filed on Jan. 16, 2015.

(51) Int. Cl.
*A61F 13/551*    (2006.01)
*A61F 13/49*    (2006.01)
(Continued)

(52) U.S. Cl.
CPC ........ *A61F 13/55105* (2013.01); *A61F 13/49* (2013.01); *A61F 13/532* (2013.01);
(Continued)

(58) Field of Classification Search
CPC .............. A61F 13/49001; A61F 13/533; A61F 13/536; A61F 13/55105; A61F 13/5511;
(Continued)

(56) References Cited

U.S. PATENT DOCUMENTS 414,637 A    11/1889    Goodson
416,794 A    12/1889    Mathieu
(Continued)

FOREIGN PATENT DOCUMENTS

EP    1 174 104    1/2002
EP    1 695 742    8/2006
(Continued)

OTHER PUBLICATIONS

"Brand Architecture Basics: What Is a Sub-Brand?" https://distility.com/building-brand/brand-architecture-basics-what-is-an-overbrand/, Sep. 27, 2011.
(Continued)

*Primary Examiner* — Tatyana Zalukaeva
*Assistant Examiner* — Gabriella E Burnette
(74) *Attorney, Agent, or Firm* — Richard L. Alexander

(57) ABSTRACT

An array of packages comprising two or more different sizes of disposable absorbent articles may comprise first and second articles comprising first and second cores having different Channel Spacings, Curvatures, Arm Angles, and/or Lengths.

20 Claims, 29 Drawing Sheets

(51) Int. Cl.
*A61F 13/532* (2006.01)
*A61F 13/537* (2006.01)
*A61F 13/53* (2006.01)

(52) U.S. Cl.
CPC .......... *A61F 13/537* (2013.01); *A61F 13/551* (2013.01); *A61F 2013/530868* (2013.01)

(58) Field of Classification Search
CPC .......... A61F 2013/15365; A61F 2013/530481; A61F 2013/5315; A61F 2013/53472; A61F 2013/5349; A61F 13/49; A61F 13/532; A61F 13/537; A61F 13/551; A61F 2013/530868
See application file for complete search history.

(56) References Cited

U.S. PATENT DOCUMENTS

| | | | |
|---|---|---|---|
| 421,901 A | 2/1890 | Breher | |
| 421,902 A | 2/1890 | Britz | |
| 437,686 A | 10/1890 | Geddes | |
| 443,451 A | 12/1890 | Hunter | |
| 443,508 A | 12/1890 | Emmet | |
| 445,329 A | 1/1891 | Kerr | |
| 451,279 A | 4/1891 | Sailor | |
| 3,815,602 A | 6/1974 | Johns et al. | |
| 3,967,756 A | 7/1976 | Barish | |
| 3,982,659 A | 9/1976 | Ross | |
| 3,994,417 A | 11/1976 | Boedecker | |
| 4,117,187 A | 9/1978 | Adams et al. | |
| 4,230,113 A | 10/1980 | Mehta | |
| 4,299,223 A | 11/1981 | Cronkrite | |
| 4,471,881 A | 9/1984 | Foster | |
| 4,706,845 A | 11/1987 | Schnurer et al. | |
| 4,840,270 A | 6/1989 | Caputo et al. | |
| 4,940,464 A | 7/1990 | Van Gompel | |
| 4,966,286 A | 10/1990 | Muckenfuhs | |
| 4,971,220 A | 11/1990 | Kaufman et al. | |
| 5,050,737 A | 9/1991 | Joslyn et al. | |
| 5,065,868 A | 11/1991 | Cornelissen et al. | |
| 5,151,092 A | 9/1992 | Buell et al. | |
| 5,231,266 A | 7/1993 | Warren | |
| 5,242,057 A | 9/1993 | Cook et al. | |
| 5,261,901 A | 11/1993 | Guay | |
| 5,284,263 A | 2/1994 | Papciak | |
| 5,322,178 A | 6/1994 | Foos | |
| 5,366,104 A | 11/1994 | Armstrong | |
| 5,368,188 A | 11/1994 | Twardowski | |
| 5,377,853 A | 1/1995 | Papciak | |
| 5,395,358 A | 3/1995 | Lu | |
| 5,413,849 A | 5/1995 | Austin et al. | |
| 5,443,161 A | 8/1995 | Jonese | |
| 5,485,919 A | 1/1996 | Samberg et al. | |
| 5,569,234 A | 10/1996 | Buell et al. | |
| 5,575,783 A | 11/1996 | Clear et al. | |
| 5,591,155 A | 1/1997 | Nishikawa et al. | |
| 5,599,620 A | 2/1997 | Huskey | |
| 5,647,506 A | 7/1997 | Julius | |
| 5,678,727 A | 10/1997 | Rice | |
| 5,690,627 A | 11/1997 | Clear et al. | |
| 5,715,841 A | 2/1998 | Utecht | |
| 5,732,716 A | 3/1998 | Utecht | |
| 5,735,839 A | 4/1998 | Kawaguchi et al. | |
| 5,746,730 A | 5/1998 | Suzuki et al. | |
| 5,785,179 A | 7/1998 | Buczwinski et al. | |
| 5,791,465 A | 8/1998 | Niki et al. | |
| 5,839,585 A | 11/1998 | Miller | |
| 5,865,322 A | 2/1999 | Miller | |
| 5,885,264 A | 3/1999 | Matsushita | |
| 5,938,648 A | 8/1999 | LaVon et al. | |
| 5,944,237 A | 8/1999 | Gouldson | |
| 5,947,302 A | 9/1999 | Miller | |
| 6,013,590 A | 1/2000 | Noda | |
| 6,024,094 A | 2/2000 | Utecht | |
| 6,050,985 A | 4/2000 | LaVon et al. | |
| 6,075,178 A | 6/2000 | Wilhelm et al. | |
| 6,092,690 A | 7/2000 | Bitowft et al. | |
| 6,168,022 B1 | 1/2001 | Ward et al. | |
| 6,190,369 B1 | 2/2001 | Palumbo et al. | |
| 6,195,800 B1 | 3/2001 | Gilmer et al. | |
| 6,229,061 B1 | 5/2001 | Dragoo et al. | |
| 6,258,077 B1 | 7/2001 | Buell et al. | |
| 6,269,969 B1 | 8/2001 | Huang et al. | |
| 6,269,970 B1 | 8/2001 | Huang et al. | |
| 6,274,218 B1 | 8/2001 | Shingo | |
| 6,296,144 B1 | 10/2001 | Tanaka et al. | |
| 6,315,114 B1 | 11/2001 | Keck et al. | |
| 6,361,784 B1 | 3/2002 | Brennan et al. | |
| 6,401,968 B1 | 6/2002 | Huang et al. | |
| 6,412,634 B1 | 7/2002 | Telesca et al. | |
| 6,454,095 B1 | 9/2002 | Brisebois et al. | |
| 6,488,202 B1 | 12/2002 | Seitz et al. | |
| 6,491,165 B2 | 12/2002 | Kuske et al. | |
| 6,500,444 B1 | 12/2002 | Ferenc et al. | |
| 6,520,946 B1 | 2/2003 | Krueger | |
| 6,568,530 B2 | 5/2003 | Takahashi et al. | |
| 6,581,775 B1 | 6/2003 | Hagopian | |
| 6,601,705 B2 | 8/2003 | Molina et al. | |
| 6,612,846 B1 | 9/2003 | Underhill et al. | |
| 6,648,864 B2* | 11/2003 | Ronn | A61F 13/84 604/385.01 |
| 6,649,808 B1 | 11/2003 | Tao | |
| 6,667,464 B2 | 12/2003 | Ellis | |
| 6,763,944 B2 | 7/2004 | Ronn et al. | |
| 6,830,755 B2 | 12/2004 | Librizzi et al. | |
| 6,837,395 B2 | 1/2005 | Windorski et al. | |
| 6,911,022 B2 | 6/2005 | Steger et al. | |
| 7,008,685 B2 | 3/2006 | Groitzsch et al. | |
| 7,222,732 B2 | 5/2007 | Ronn et al. | |
| 7,549,538 B2 | 6/2009 | Naoe et al. | |
| 7,572,249 B2 | 8/2009 | Betts | |
| 7,582,075 B2 | 9/2009 | Betts et al. | |
| 7,770,729 B2 | 8/2010 | Warren et al. | |
| 7,824,389 B2 | 11/2010 | Veith | |
| 7,863,497 B2 | 1/2011 | Magee et al. | |
| 7,931,632 B2 | 4/2011 | Betts | |
| 7,959,621 B2 | 6/2011 | Ashton et al. | |
| 7,998,127 B2 | 8/2011 | Betts | |
| 8,069,982 B2 | 12/2011 | Ronn et al. | |
| 8,079,994 B2 | 12/2011 | Richlen | |
| 8,092,438 B2 | 1/2012 | Betts et al. | |
| 8,220,632 B2 | 7/2012 | Oi et al. | |
| 8,226,625 B2 | 7/2012 | Turner et al. | |
| 8,273,067 B2 | 9/2012 | Cohen | |
| 8,388,594 B2 | 3/2013 | Turner et al. | |
| 8,435,222 B2 | 5/2013 | Ronn et al. | |
| 8,480,642 B2 | 7/2013 | Betts | |
| 8,518,004 B2 | 8/2013 | Betts et al. | |
| 8,568,566 B2* | 10/2013 | Jackels | A61F 13/15658 162/297 |
| 8,834,436 B2 | 9/2014 | Ronn et al. | |
| 9,028,462 B2 | 5/2015 | Poole et al. | |
| 9,039,669 B1 | 5/2015 | LaVon et al. | |
| 9,216,118 B2 | 12/2015 | Roe et al. | |
| 9,254,228 B2 | 2/2016 | Ashton | |
| 9,474,657 B2 | 10/2016 | Berrizbeitia et al. | |
| 9,622,922 B2 | 4/2017 | Nelson | |
| 9,649,232 B2 | 5/2017 | Hippe et al. | |
| 10,034,801 B2* | 7/2018 | Seitz | A61F 13/5511 |
| 2001/0021833 A1 | 9/2001 | Schmidt et al. | |
| 2001/0055609 A1 | 12/2001 | Shantz et al. | |
| 2002/0004527 A1 | 1/2002 | Auestad et al. | |
| 2002/0064323 A1 | 5/2002 | Chin | |
| 2002/0072723 A1 | 6/2002 | Ronn et al. | |
| 2002/0148742 A1 | 10/2002 | Bisbal et al. | |
| 2002/0164910 A1 | 11/2002 | Murray | |
| 2002/0173767 A1 | 11/2002 | Popp et al. | |
| 2002/0177829 A1 | 11/2002 | Fell et al. | |
| 2002/0183712 A1 | 12/2002 | Datta et al. | |
| 2003/0019508 A1 | 1/2003 | Tomarchio et al. | |
| 2003/0073966 A1 | 4/2003 | Sosalla | |
| 2003/0097109 A1 | 5/2003 | Bruce | |
| 2003/0114808 A1 | 6/2003 | Underhill et al. | |
| 2003/0120231 A1 | 6/2003 | Wang et al. | |

(56) References Cited

U.S. PATENT DOCUMENTS

| | | |
|---|---|---|
| 2003/0135186 A1 | 7/2003 | Olson et al. |
| 2003/0136704 A1 | 7/2003 | Burgess |
| 2003/0139713 A1 | 7/2003 | Olson et al. |
| 2003/0158532 A1 | 8/2003 | Magee et al. |
| 2003/0181883 A1 | 9/2003 | Olson et al. |
| 2003/0226266 A1 | 12/2003 | Ellis |
| 2003/0229327 A1 | 12/2003 | Imsangjan et al. |
| 2004/0006323 A1 | 1/2004 | Hall et al. |
| 2004/0010240 A1 | 1/2004 | Ronn et al. |
| 2004/0030308 A1 | 2/2004 | Ronn et al. |
| 2004/0030317 A1 | 2/2004 | Torigoshi et al. |
| 2004/0052834 A1 | 3/2004 | West et al. |
| 2004/0064126 A1 | 4/2004 | Fletcher |
| 2004/0087928 A1 | 5/2004 | Ducker |
| 2004/0092904 A1 | 5/2004 | De, Jr. et al. |
| 2004/0097897 A1 | 7/2004 | Ronn et al. |
| 2004/0127865 A1 | 7/2004 | Mitsui et al. |
| 2004/0162536 A1 | 8/2004 | Becker et al. |
| 2004/0219854 A1 | 11/2004 | Groitzsch et al. |
| 2004/0243083 A1 | 12/2004 | Matsuda et al. |
| 2004/0249354 A1 | 12/2004 | Matsuda et al. |
| 2005/0059943 A1 | 3/2005 | Suzuki et al. |
| 2005/0065492 A1 | 3/2005 | Cole et al. |
| 2005/0074483 A1 | 4/2005 | Lange |
| 2005/0085782 A1 | 4/2005 | Popp et al. |
| 2005/0102735 A1 | 5/2005 | Popp et al. |
| 2005/0121347 A1 | 6/2005 | Hanson |
| 2005/0133387 A1 | 6/2005 | Cohen et al. |
| 2005/0142336 A1 | 6/2005 | Romano, III et al. |
| 2005/0148983 A1 | 7/2005 | Doverbo et al. |
| 2005/0210566 A1 | 9/2005 | Mortell et al. |
| 2005/0256493 A1 | 11/2005 | Datta et al. |
| 2005/0256758 A1 | 11/2005 | Sierra et al. |
| 2005/0267431 A1 | 12/2005 | Sasaki et al. |
| 2006/0052763 A1 | 3/2006 | Tachibana |
| 2006/0069372 A1 | 3/2006 | Chakravarty |
| 2006/0082133 A1 | 4/2006 | Naoe et al. |
| 2006/0173695 A1 | 8/2006 | Brandt |
| 2006/0183086 A1 | 8/2006 | Brandt |
| 2006/0186132 A1 | 8/2006 | Panning et al. |
| 2006/0193898 A1 | 8/2006 | Norman |
| 2006/0195357 A1 | 8/2006 | Klofta et al. |
| 2006/0229581 A1 | 10/2006 | Ulas et al. |
| 2006/0241558 A1 | 10/2006 | Ramshak |
| 2007/0016158 A1 | 1/2007 | Endres |
| 2007/0032768 A1 | 2/2007 | Cohen et al. |
| 2007/0043331 A1 | 2/2007 | Haruki et al. |
| 2007/0141311 A1 | 6/2007 | Mleziva et al. |
| 2007/0142798 A1 | 6/2007 | Goodlander et al. |
| 2007/0151182 A1 | 7/2007 | Ronn et al. |
| 2007/0255248 A1 | 11/2007 | Hendren et al. |
| 2007/0287975 A1 | 12/2007 | Fujimoto et al. |
| 2007/0293833 A1 | 12/2007 | Wennerback |
| 2008/0051747 A1 | 2/2008 | Cohen |
| 2008/0082070 A1 | 4/2008 | Fell et al. |
| 2008/0110782 A1 | 5/2008 | Burgdorf et al. |
| 2008/0128308 A1 | 6/2008 | Betts |
| 2008/0195070 A1 | 8/2008 | Ponomarenk et al. |
| 2008/0208155 A1 | 8/2008 | LaVon et al. |
| 2008/0234643 A1 | 9/2008 | Kaneda |
| 2009/0030389 A1 | 1/2009 | Ashton et al. |
| 2009/0088718 A1 | 4/2009 | Toyoshima et al. |
| 2009/0240221 A1 | 9/2009 | Rothenberger et al. |
| 2009/0326504 A1 | 12/2009 | Kaneda |
| 2010/0057029 A1 | 3/2010 | Popp et al. |
| 2010/0106123 A1 | 4/2010 | Fukae |
| 2010/0108554 A1 | 5/2010 | Melius et al. |
| 2010/0130956 A1 | 5/2010 | Wennerback |
| 2010/0181223 A1 | 7/2010 | Warren et al. |
| 2010/0292666 A1 | 11/2010 | Olson et al. |
| 2011/0077609 A1 | 3/2011 | Kuwano et al. |
| 2011/0088828 A1 | 4/2011 | Misek et al. |
| 2011/0098668 A1 | 4/2011 | Thorson et al. |
| 2011/0144602 A1 | 6/2011 | Long |
| 2011/0160687 A1 | 6/2011 | Welch et al. |
| 2011/0288517 A1 | 11/2011 | Mori |
| 2012/0083758 A1 | 4/2012 | Ronn et al. |
| 2012/0215191 A1 | 8/2012 | Takino |
| 2012/0271267 A1 | 10/2012 | Love et al. |
| 2012/0296293 A1 | 11/2012 | Clifford |
| 2013/0018351 A1 | 1/2013 | Desai |
| 2013/0041340 A1 | 2/2013 | Kawakami et al. |
| 2013/0072887 A1 | 3/2013 | LaVon et al. |
| 2013/0138072 A1 | 5/2013 | Morimoto et al. |
| 2013/0165895 A1 | 6/2013 | Wennerback |
| 2013/0211355 A1 | 8/2013 | Nishikawa et al. |
| 2013/0211356 A1 | 8/2013 | Nishikawa et al. |
| 2013/0211357 A1 | 8/2013 | Nishikawa et al. |
| 2013/0211363 A1 | 8/2013 | LaVon et al. |
| 2013/0226127 A1 | 8/2013 | Takahashi et al. |
| 2013/0233749 A1 | 9/2013 | Ronn et al. |
| 2013/0281954 A1 | 10/2013 | Ishihara et al. |
| 2013/0306226 A1 | 11/2013 | Zink et al. |
| 2013/0310795 A1 | 11/2013 | Glahn et al. |
| 2014/0013490 A1 | 1/2014 | Evenson et al. |
| 2014/0018759 A1 | 1/2014 | Jayasinghe et al. |
| 2014/0163506 A1 * | 6/2014 | Roe ................... A61F 13/49001 604/378 |
| 2014/0171892 A1 | 6/2014 | Ichikawa et al. |
| 2014/0224695 A1 | 8/2014 | Ronn et al. |
| 2014/0288519 A1 | 9/2014 | Schmitz et al. |
| 2014/0288523 A1 | 9/2014 | Hasse et al. |
| 2014/0350508 A1 | 11/2014 | Popp et al. |
| 2014/0371701 A1 | 12/2014 | Bianichi |
| 2014/0378932 A1 | 12/2014 | Seitz et al. |
| 2015/0065982 A1 | 3/2015 | Hamilton |
| 2015/0320613 A1 | 4/2015 | Seitz |
| 2015/0320621 A1 | 7/2015 | Seitz |
| 2015/0283004 A1 | 10/2015 | Seitz |
| 2015/0320611 A1 | 11/2015 | Seitz |
| 2015/0320612 A1 * | 11/2015 | Seitz ................. A61F 13/49017 604/385.01 |
| 2015/0320614 A1 | 11/2015 | Seitz |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een et al. |
| 2016/0058627 A1 | 3/2016 | Barnes et al. |
| 2016/0095764 A1 | 4/2016 | Seitz |
| 2016/0100989 A1 | 4/2016 | Seitz |
| 2016/0100995 A1 | 4/2016 | Seitz |
| 2016/0100996 A1 | 4/2016 | Seitz |
| 2016/0100997 A1 | 4/2016 | Seitz |
| 2016/0100999 A1 | 4/2016 | Seitz |
| 2016/0136004 A1 | 5/2016 | LaVon et al. |
| 2017/0049637 A1 | 2/2017 | Mori et al. |
| 2017/0128285 A1 | 5/2017 | Seitz |

FOREIGN PATENT DOCUMENTS

| | | | |
|---|---|---|---|
| EP | 2314261 | 4/2011 | |
| EP | 2979671 A1 * | 2/2016 | ......... A61F 13/4756 |
| GB | 1 603 780 | 11/1981 | |
| JP | H11-21702 | 1/1999 | |
| JP | 3046066 | 5/2000 | |
| JP | 2003-285890 | 1/2002 | |
| JP | 2003-070838 | 3/2003 | |
| JP | 2004-057640 | 2/2004 | |
| JP | 2008253290 | 10/2008 | |
| WO | WO-1999/055213 | 11/1999 | |
| WO | WO-2000/027268 | 5/2000 | |
| WO | WO-2002/014172 | 2/2002 | |
| WO | WO 2005/039511 | 5/2005 | |
| WO | WO2008123348 | 10/2008 | |

OTHER PUBLICATIONS

Advertisements: "Introducing Pampers Phases", Sep. 1991.
"Introducing New! Luvs Phases", Jan. 1992.
"Introducing! The First Specially Designed Diaper Made Just for Your Walker", Sep. 1991.
"Dial-A-Wheel", Sep. 1991.
Photographs of Huggies Baby Steps Size 4 (1993).

(56) References Cited

OTHER PUBLICATIONS

Photographs of Huggies Baby Steps Size 3 (1990s).
Photographs of Huggies Baby Steps Size 4 (1991).
Photographs of Huggies Baby Steps Size 3 (1991).
Photographs of Huggies Ultratrim Size 4 (1992).
Photographs of Huggies Ultratrim Size 4 (1996).
Photographs of Huggies Ultratrim Size 2 SM/MED (1996).
Photographs of Huggies Ultratrim Size 1 Small (1996).
Photographs of Huggies Newborn (1996).
Photographs of Kleenex Newborn (1979).
Photographs of Kleenex (1980s).
Photographs of Pampers Custom Fit (2001).
Photographs of Pampers Phases Walker 2 (1993).
Photographs of Pampers Phases Infant 1 (1993).
Photographs of Pampers Phases Medium (1994).
Huggies Baby Steps Advertisement (copyrighted 1991).
International Search Report and Written Opinion, PCT/US2015/013530, dated Apr. 21, 2016.
All Office Actions, Responses and Claims, U.S. Appl. No. 14/309,129.
All Office Actions, Responses and Claims, U.S. Appl. No. 14/680,186.
All Office Actions, Responses and Claims, U.S. Appl. No. 14/698,924.
All Office Actions, Responses and Claims, U.S. Appl. No. 14/698,968.
All Office Actions, Responses and Claims, U.S. Appl. No. 14/699,011.
All Office Actions, Responses and Claims, U.S. Appl. No. 14/805,601.
All Office Actions, Responses and Claims, U.S. Appl. No. 15/879,464.
All Office Actions, Responses and Claims, U.S. Appl. No. 14/699,097.
All Office Actions, Responses and Claims, U.S. Appl. No. 14/699,123.
All Office Actions, Responses and Claims, U.S. Appl. No. 14/805,673.
All Office Actions, Responses and Claims, U.S. Appl. No. 16/059,313.
All Office Actions, Responses and Claims, U.S. Appl. No. 14/699,145.
All Office Actions, Responses and Claims, U.S. Appl. No. 14/805,700.
All Office Actions, Responses and Claims, U.S. Appl. No. 16/022,885.
All Office Actions, Responses and Claims, U.S. Appl. No. 14/878,037.
All Office Actions, Responses and Claims, U.S. Appl. No. 14/809,324.
All Office Actions, Responses and Claims, U.S. Appl. No. 14/809,334.
All Office Actions, Responses and Claims, U.S. Appl. No. 14/878,142.
All Office Actions, Responses and Claims, U.S. Appl. No. 14/878,156.
All Office Actions, Responses and Claims, U.S. Appl. No. 14/996,683.
All Office Actions, Responses and Claims, U.S. Appl. No. 15/343,787.
All Office Actions, Responses and Claims, U.S. Appl. No. 16/023,487.
All Office Actions, Responses and Claims, U.S. Appl. No. 16/023,569.
All Office Actions, Responses and Claims, U.S. Appl. No. 16/023,766.
All Office Actions, Responses and Claims, U.S. Appl. No. 16/023,809.
All Office Actions, Responses and Claims, U.S. Appl. No. 16/023,830.

* cited by examiner

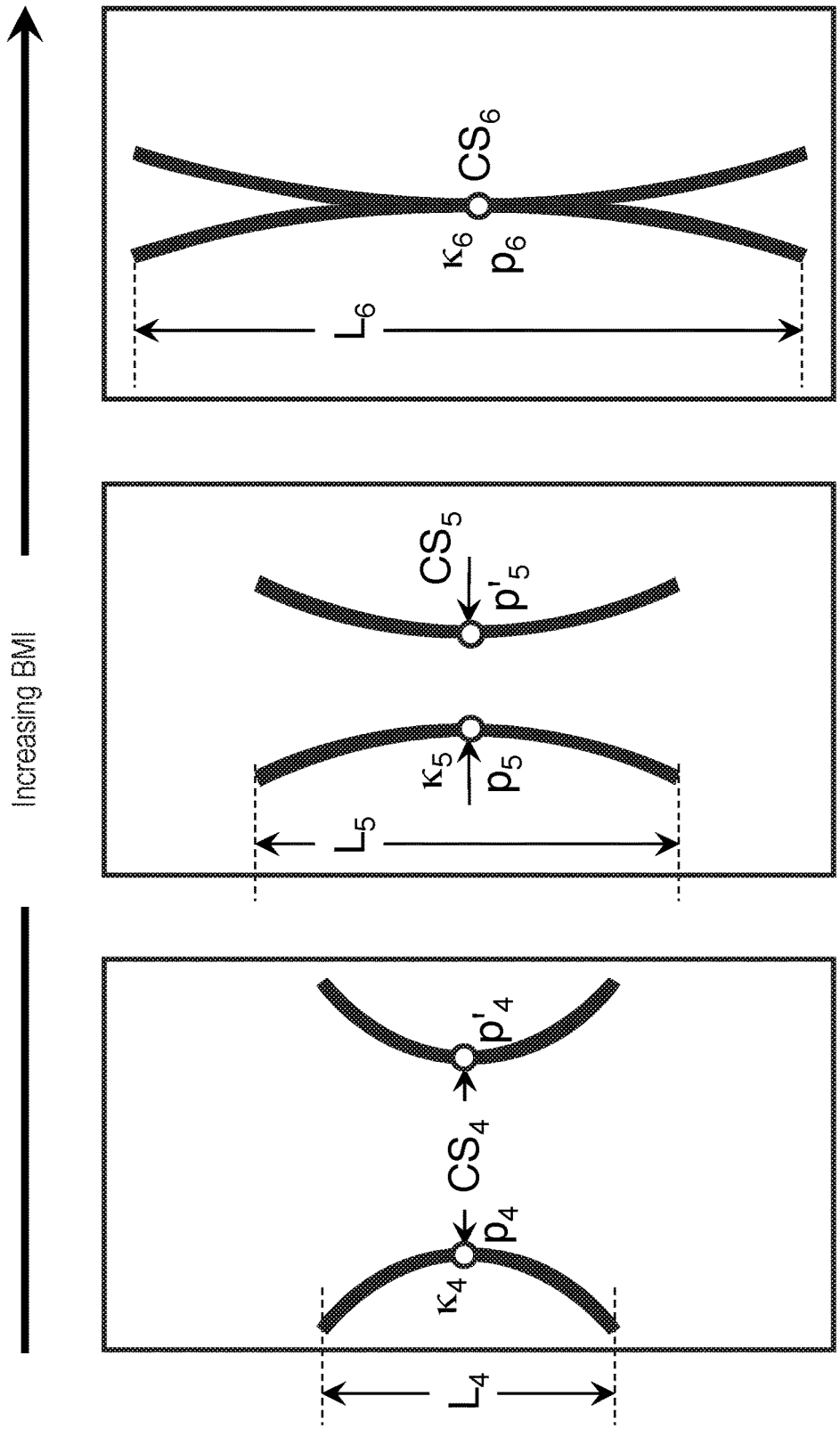

Always Discreet Underwear

| Size | Waist (in) | Weight (lbs) |
|---|---|---|
| S/M | 28-40 | 115-190 |
| L | 35-50 | 170-260 |
| XL | 48-64 | 200-300 |

⇩

Establishing the Target BMI

| Target Waist (in) | Target Waist (mm) | Target Weight (lbs) | Target Weight (kg) | Target BMI from Waist (kg/m2) | Target BMI from Weight (kg/m2) | Target BMI (kg/m2) |
|---|---|---|---|---|---|---|
| 34 | 864 | 153 | 69.2 | 26.8 | 27.0 | 26.8 |
| 43 | 1080 | 215 | 97.5 | 34.6 | 37.0 | 34.6 |
| 56 | 1422 | 250 | 113.4 | 47.5 | 42.9 | 47.5 |

Fig. 26

Depend for Women Underwear

| Size | Waist (in) | Hip (in) | Weight (lbs) |
|---|---|---|---|
| S/M | 28-40 | 34-46 | 115-190 |
| L | 38-50 | 44-54 | 170-260 |
| XL | 48-64 | 48-64 | 200-300 |

⇩

Establishing the Target BMI

| Target Waist (in) | Target Waist (mm) | Target Hip (in) | Target Hip (mm) | Target Weight (lbs) | Target Weight (kg) | Target BMI from Waist (kg/m2) | Target BMI from Hip (kg/m2) | Target BMI from Weight (kg/m2) | Target BMI (kg/m2) |
|---|---|---|---|---|---|---|---|---|---|
| 34 | 864 | 40 | 1016 | 153 | 69.2 | 26.8 | 26.8 | 27.0 | 26.8 |
| 44 | 1118 | 49 | 1245 | 215 | 97.5 | 36.0 | 37.8 | 37.0 | 36.0 |
| 56 | 1422 | 56 | 1422 | 250 | 113.4 | 47.5 | 46.5 | 42.9 | 47.5 |

Fig. 27

Depend Silhouette Briefs for Women

| Size | Waist (in) | Hip (in) | Weight (lbs) |
|---|---|---|---|
| S/M | 28-40 | 34-46 | 115-190 |
| L/XL | 38-50 | 44-54 | 170-300 |

Establishing the Target BMI

| Target Waist (in) | Target Waist (mm) | Target Hip (in) | Target Hip (mm) | Target Weight (lbs) | Target Weight (kg) | Target BMI from Waist (kg/m2) | Target BMI from Hip (kg/m2) | Target BMI from Weight (kg/m2) | Target BMI (kg/m2) |
|---|---|---|---|---|---|---|---|---|---|
| 34 | 864 | 40 | 1016 | 153 | 69.2 | 26.8 | 26.8 | 27.0 | 26.8 |
| 44 | 1118 | 49 | 1245 | 235 | 106.6 | 36.0 | 37.8 | 40.4 | 36.0 |

Fig. 28

| Women's Panty Size Chart | | |
|---|---|---|
| Size | Waist (in) | Hips (in) |
| 4 (XS) | 23-24 | 33-34 |
| 5 (S) | 25-26 | 35-36 |
| 6 (M) | 27-28 | 37-38 |
| 7 (L) | 29-30 | 39-40 |
| 8 (XL) | 31-32 | 41-42 |
| 9 (2XL) | 33-34 | 43-44 |
| 10 (3XL) | 35-36 | 45-46 |
| 11 (4XL) | 37-38 | 47-48 |
| 12 (5XL) | 39-40 | 49-50 |
| 13 (6XL) | 41-42 | 51-52 |
| 14 (7XL) | 43-44 | 53-54 |
| 15 (8XL) | 45-46 | 55-56 |

| Establishing the Target BMI | | | | | | |
|---|---|---|---|---|---|---|
| Target Waist (in) | Target Waist (mm) | Target Hip (in) | Target Hip (mm) | Target BMI from Waist (kg/m²) | Target BMI from Hip (kg/m²) | Target BMI (kg/m²) |
| 23.5 | 597 | 33.5 | 851 | 17.4 | 19.0 | 17.4 |
| 25.5 | 648 | 35.5 | 902 | 19.1 | 21.4 | 19.1 |
| 27.5 | 699 | 37.5 | 953 | 20.9 | 23.7 | 20.9 |
| 29.5 | 749 | 39.5 | 1003 | 22.7 | 26.2 | 22.7 |
| 31.5 | 800 | 41.5 | 1054 | 24.5 | 28.6 | 24.5 |
| 33.5 | 851 | 43.5 | 1105 | 26.3 | 31.0 | 26.3 |
| 35.5 | 902 | 45.5 | 1156 | 28.1 | 33.5 | 28.1 |
| 37.5 | 953 | 47.5 | 1207 | 30.0 | 35.9 | 30.0 |
| 39.5 | 1003 | 49.5 | 1257 | 31.8 | 38.4 | 31.8 |
| 41.5 | 1054 | 51.5 | 1308 | 33.7 | 40.9 | 33.7 |
| 43.5 | 1105 | 53.5 | 1359 | 35.6 | 43.4 | 35.6 |
| 45.5 | 1156 | 55.5 | 1410 | 37.4 | 45.9 | 37.4 |

ADULT DISPOSABLE ABSORBENT ARTICLES AND ARRAYS OF SAID ARTICLES COMPRISING ABSORBENT CORES HAVING CHANNELS

CROSS REFERENCE TO RELATED APPLICATIONS

This application claims the benefit, under 35 USC 119(e), to U.S. Provisional Patent Application No. 62/104,330 filed on Jan. 16, 2015, which is herein incorporated by reference in its entirety.

FIELD

The present disclosure is directed to disposable absorbent articles and arrays of disposable absorbent articles which are designed to fit different adult body sizes, shapes and types, and as such are sized to fit a broad range of adult consumers.

BACKGROUND

Adult incontinence ("AI") articles are designed to absorb and contain liquid and other discharges from the human body to prevent the body and clothing from becoming soiled. One challenge is to provide a line-up of AI articles that meets the urine containment needs while providing an article that meets the fit and comfort desires of diverse wearers, which can range over several hundred pounds. These challenges include bulkiness and stiffness of the absorbent core, in both the dry and wet state.

In recent years, absorbent core designs have progressed toward structures with relatively higher proportions by weight of absorbent polymer particles and lower proportions of absorbent fiber (e.g., cellulose fiber), resulting in structures that are thinner than absorbent core designs of earlier years and enabling manufacture of products that are less bulky when dry. The latter structures, however, can be slower in liquid acquisition rate, and because of their greater proportions of absorbent polymer particles, can become saggy, bulky and gelatinous when wetted. To address these issues, absorbent structures including longitudinally-oriented channels have been developed (hereafter referred to as channels).

Appropriately located and structured longitudinal channels can help distribute liquid along deposits of absorbent polymer particles along the length of the absorbent core, and thereby help improve acquisition rate. They also can help reduce chances of a saggy and bulky appearance of the article when wetted by providing longitudinal structural rigidity through the crotch region of the article resulting from pressure within the wetted absorbent polymer particle deposits between the channels. They also help by providing natural hinge zones, which can minimize the appearance of bulk while improving overall comfort to the wearer.

Examples of channels suitable for use with articles of the present disclosure are disclosed in WO2012/170778 (Rosati et al., see also WO2012/170779, WO2012/170781 and WO2012/170808), further in WO2014/093319, WO2014/093311 (both Arizti) and WO2014/093310 (Ehrnsperger). The material free zone in these disclosures may be curved. Other prior art discloses channels that are straight, and typically oriented in the longitudinal and/or transverse direction of the core, as in WO95/11652 (Tanzer) or WO2012/052,172A1 (Van Malderen).

There is a need to improve fit and comfort of absorbent articles. Providing absorbent articles of different dimensions (in longitudinal and transversal direction) based on the body dimensions to provide the right coverage and performance is known. The present inventors have now found that the channel dimensions and shape as well as position of the channels within an array of articles should be specifically adapted to the size of the wearer. Adapting the dimensions of the channels to BMI driven morphological changes (leg and crotch shape) is beneficial to enable proper fit and comfort along the full range of consumers. In addition, the inventors have found a correlation between channel dimensions, shape and position and BMI driven morphological changes (i.e., like leg and crotch shape) that can be used to improve fit and comfort for a given sizes of articles in an array. In short, the geometry of the channels should be adapted to the BMI of the wearer to provide for better fit and comfort.

Body Mass Index (BMI) is on the rise globally for both men and women. In the U.S. alone, more than ⅓ of adult females are now considered obese (BMI>30). This has changed significantly over the past 30 years; in 1980 only about 16% of U.S. adult females were obese. Larger women exhibit different ratios of body anthropometrics than smaller women, i.e., all body dimensions do not simply scale-up as women get larger. In addition, women across the range of BMI may also have very different body shapes. There is a lack of recognition and understanding of this issue by current adult absorbent article manufacturers and as such consumers' needs are not being adequately met. Therefore, there is a need to develop adult absorbent articles for a wide variety of body shapes and sizes in order to provide an improved level of fit and contact between the body and the adult absorbent article to reduce the occurrence of leakage and improve the overall fit, comfort, coverage and discretion of the article. There is a clear need for adult absorbent articles which are designed for variety of wearers based on their BMI and body shape. There is also a need to communicate to wearers the benefits of such customized adult absorbent articles in an easy-to-understand manner (e.g., some women may not understand what BMI is or know their BMI number), which is not off-putting (e.g., without stigmatizing or embarrassing women based on their BMI).

Thus, it is an object of the present disclosure to describe absorbent articles and arrays of absorbent articles whereby the channels are integrated into the absorbent articles and are designed to meet the consumer needs across the BMI range wherein each size in the array is intended to fit, both when the pant is dry and after it is wetted.

BRIEF DESCRIPTION OF THE DRAWINGS

FIGS. 10a-c show different examples of core channels for consumers of differing BMI's.

FIG. 26 is a table illustrating how the Target BMI is determined for absorbent articles where a waist range and a weight range are recommended.

FIG. 27 is a table illustrating how the Target BMI is determined for absorbent articles where a waist range, a hip range and a weight range are recommended.

FIG. 28 is a table illustrating how the Target BMI is determined for absorbent articles where a waist range, a hip range and a weight range are recommended.

DETAILED DESCRIPTION

"Pull-on garment" or "pant" means articles of wear which have a defined waist opening and a pair of leg openings and which are typically pulled onto the body of the wearer by inserting the legs into the leg openings and pulling the article up over the waist.

"Disposable" means garment, which are not intended to be laundered or otherwise restored or reused as a garment (i.e., they are intended to be discarded after a single use and to be recycled, composted or otherwise disposed of in an environmentally compatible manner). The pull-on garment may be "absorbent" such that it absorbs and contains the various exudates discharged from the body.

Figure 20:
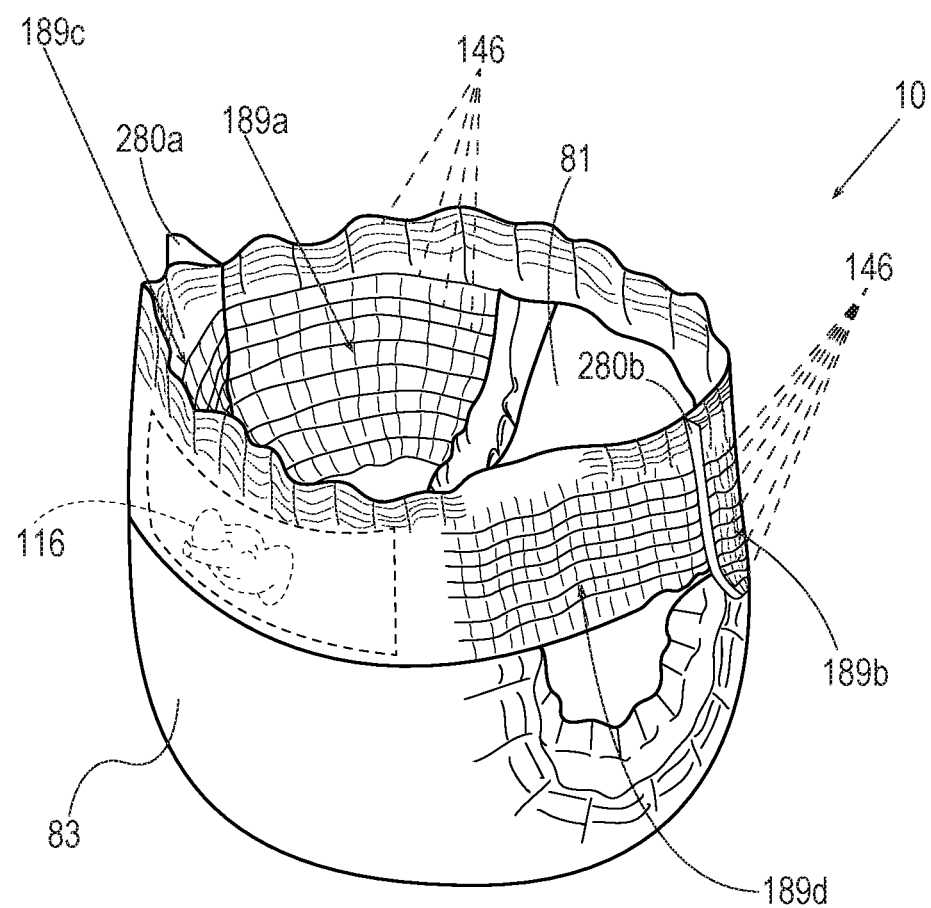
FIG. 20 is a perspective view of the pant diaper shown in FIG. 1 wherein belts connect opposing waist regions.
Figure 21:
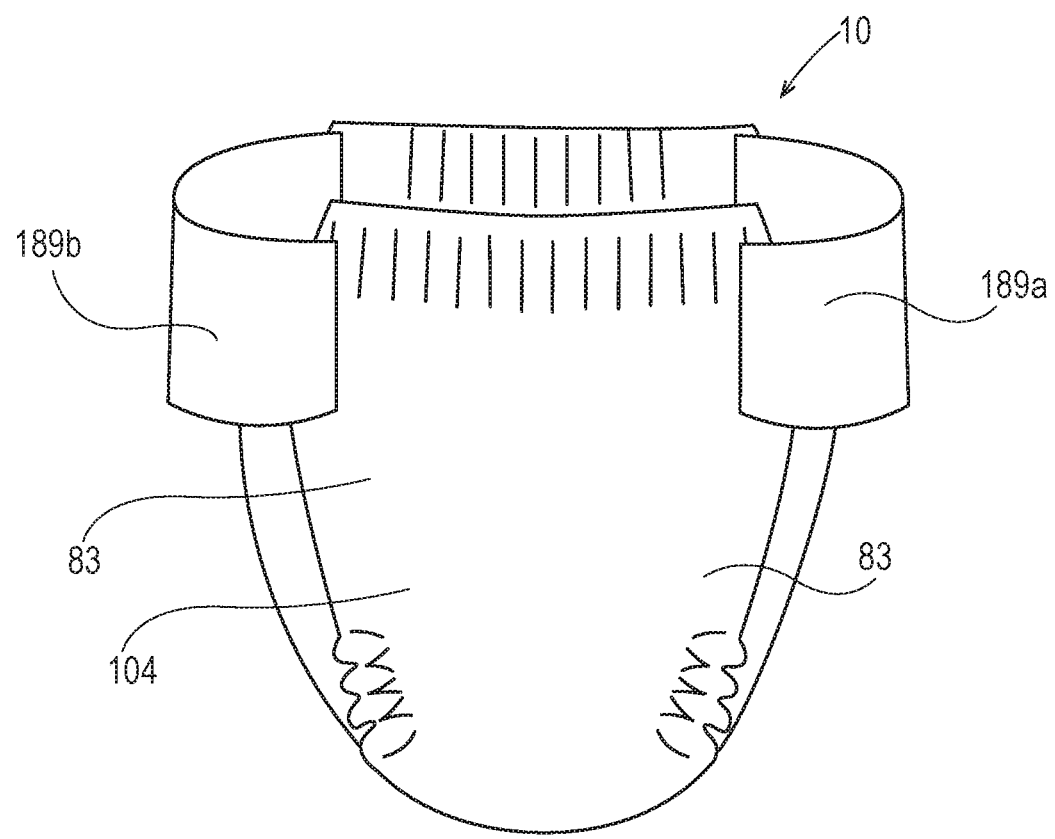
FIG. 21 is a perspective view of the pant diaper shown in FIG. 18 wherein flaps connect opposing waist regions.
Figure 22:
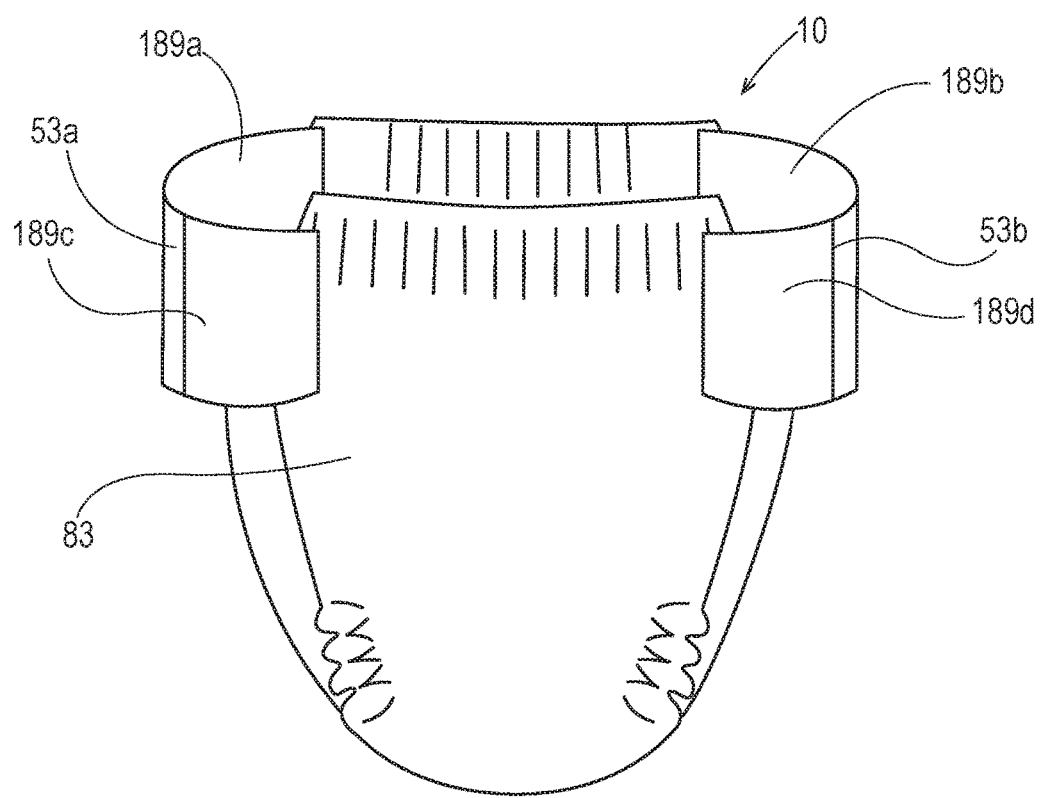
FIG. 22 is a perspective view of the pant diaper shown in FIG. 19 wherein side seams connect the flaps and opposing waist regions.

"Closed form" means opposing waist regions are joined to form a continuous waist opening and leg openings. See, for example, FIGS. 20-22.

"Array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material." Furthermore, the packaging is distinctly different in that "for Women Underwear" is packaged in a predominately green, film bag and "Silhouette For Women" is packaged in a predominately maroon box.

Further regarding "Arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material." Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

"On-line Array" means an "Array" distributed by a common on-line source.

"Thigh Spacing" means the narrowest lateral distance between the thighs at a point, which is parallel to the coronal plane and on the horizontal plane defined at the Gluteal Sulcus (the gluteal sulcus is often referred to as the fold of the buttock or the gluteal fold of the horizontal gluteal crease). This is illustrated in FIG. 2 and in FIG. 3 at plane B:B of FIG. 2.

Figure 2:
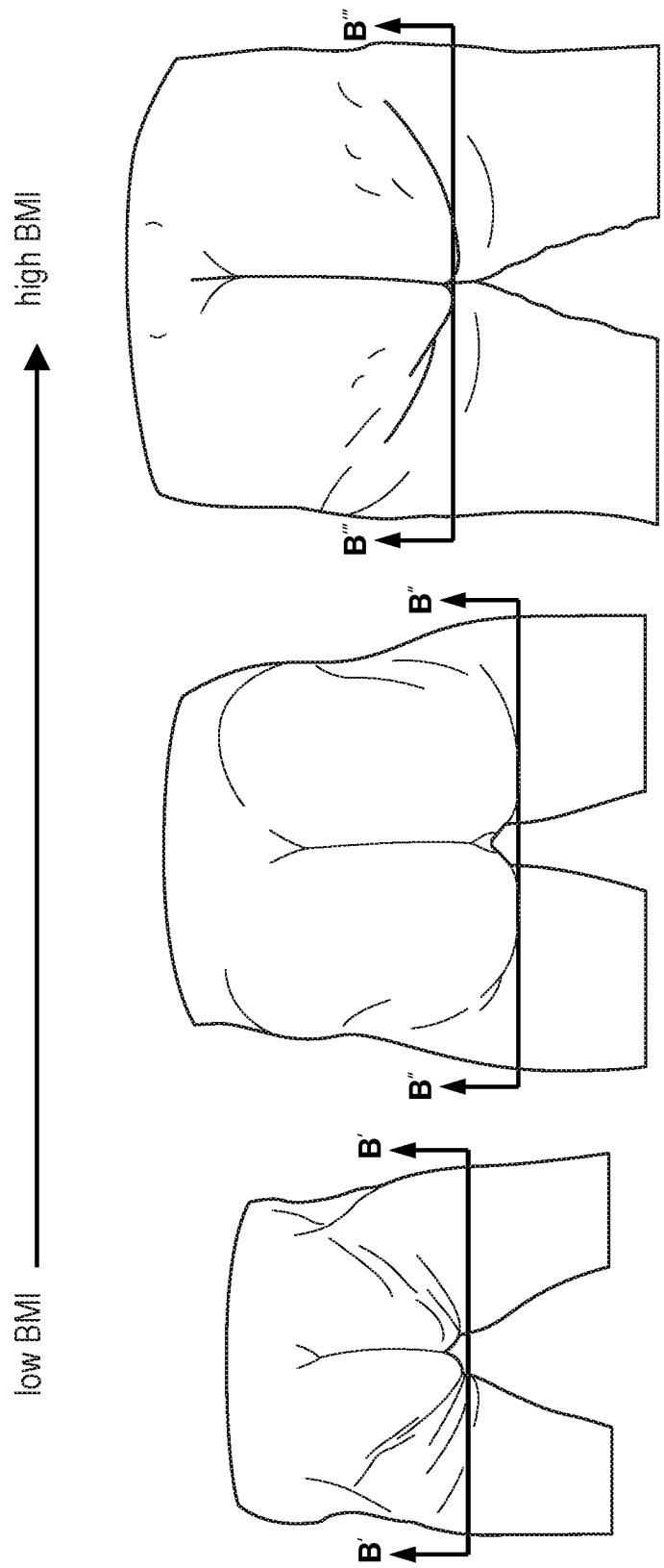
FIG. 2 shows representative female body shapes of differing BMI where the transverse plane B:B is determined at the gluteal sulcus.
Figure 3:
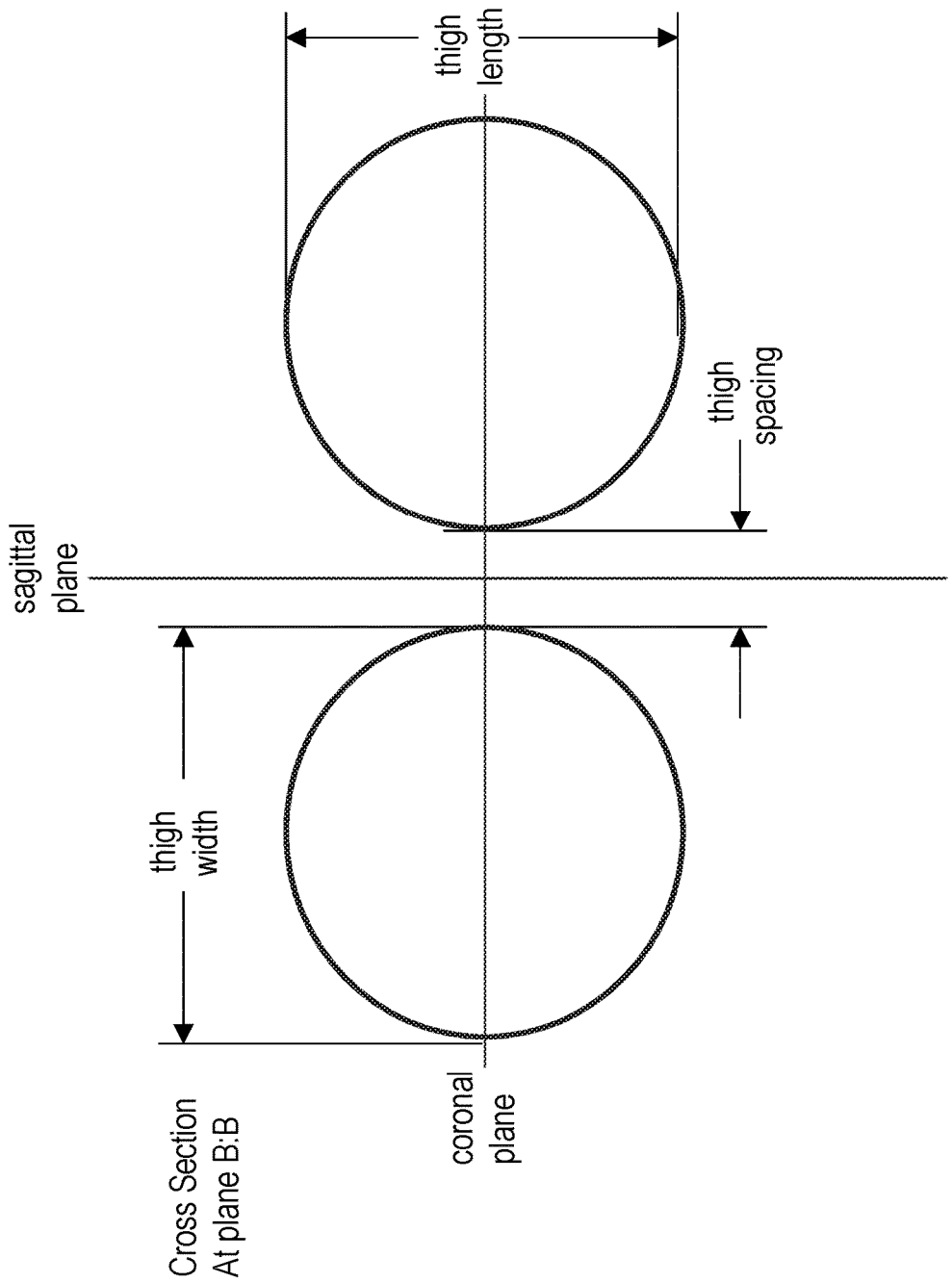
FIG. 3 shows representative female morphological measurements taken at plane B:B of FIG. 2, including thigh spacing, thigh diameter parallel to the sagittal plane (thigh length), and thigh diameter parallel to the coronal plane (thigh width).

"Thigh Eccentricity" is the approximate eccentricity of the thigh at plane B:B of FIG. 2, where plane B:B is described above. Hereafter, Thigh Eccentricity is considered negative when the major axis of the thigh cross section at plane B:B is perpendicular to the coronal plane of the body. The thigh's major axis is the larger of either the Thigh Width, or Thigh Length as illustrated in FIG. 3.

Figure 9A:
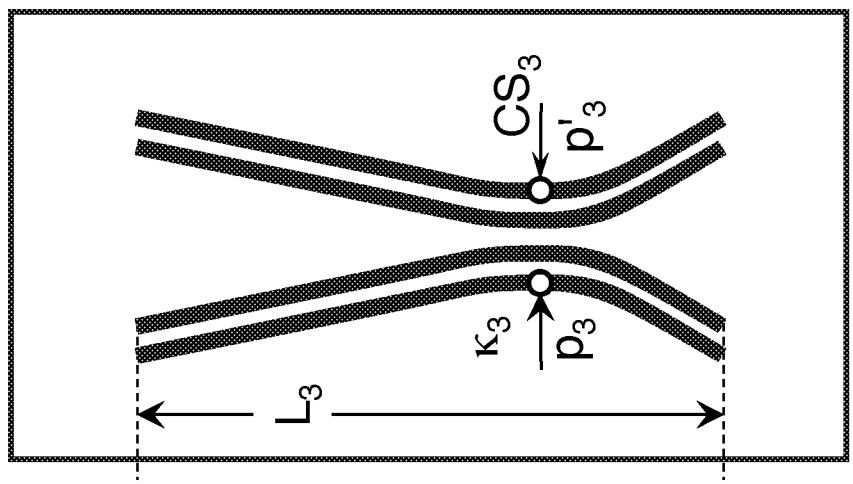
FIGS. 9a-c show different examples of channels and how various channel parameters are determined.
Figure 9B:
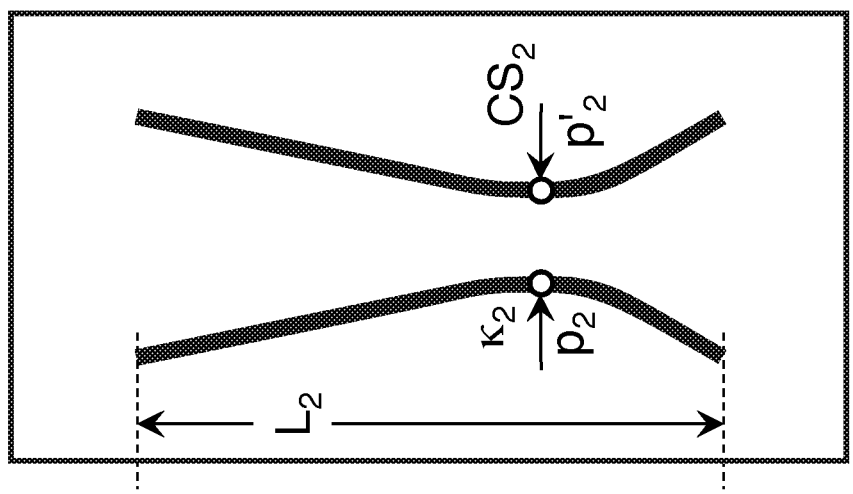
Figure 9C:
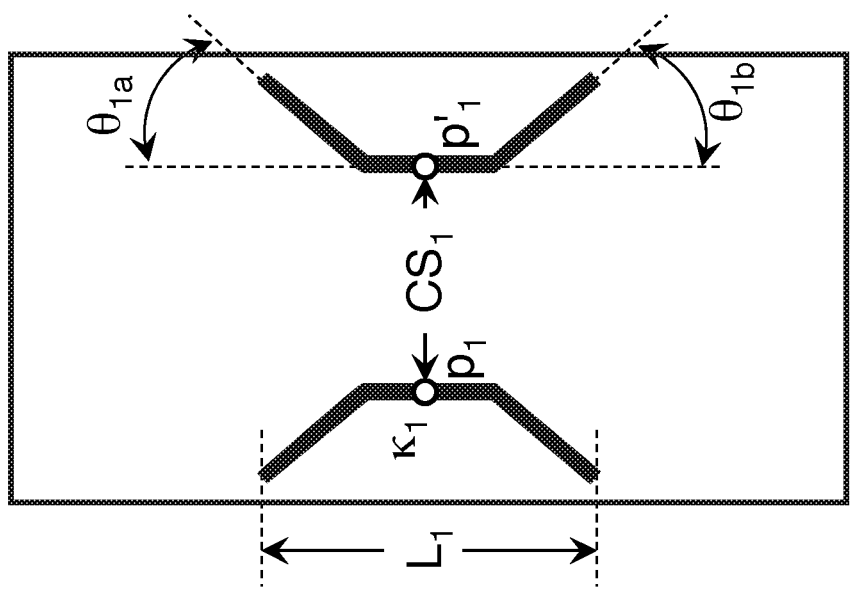

"Channel Spacing," hereafter denoted as CS means the minimum lateral distance between two longitudinally extending laterally spaced channels. This is illustrated in FIG. 9. FIG. 9a shows how CS is determined when the channels are longitudinally straight and parallel at the narrowest point within the crotch region, denoted as the distance between points $p_1$ and $p'_1$. FIG. 9b shows how CS is determined with the channels are curved or not parallel at the narrowest lateral point within the crotch region, denoted as the distance between points $p_2$ and $p'_2$. And FIG. 9c shows how CS is determined when there are more than two longitudinally extending channels, denoted as the distance between points $p_3$ and $p'_3$. In such cases, points $p_3$ and $p'_3$ are disposed in the crotch region at the narrowest lateral point between the two laterally opposing channels having the greatest Channel Length.

"Channel Curvature," hereafter denoted as κ means the curvature (inverse of the radius) at the narrowest points in the channel within the crotch region used in determining CS (denoted by points p as shown in FIG. 9.). FIG. 9a illustrates that in the case when the channels are longitudinally straight and parallel the points where CS is determined, $κ_1$ is equal to 0 (radius is equal to ∞).

"Channel Arm Angle," hereafter denoted as θ, means the angle of the arm(s) for channels that are longitudinal straight and parallel in the longitudinal mid region, and have one or more channel sections which deviate from the straight sections. This is illustrated in FIG. 9a. The Channel Arm Angles are denoted as $θ_{1a}$ and $θ_{1b}$.

"Channel Length" hereafter denoted as L, means the maximum longitudinal length of a channel. This is illustrated in FIG. 9a by $L_1$, in FIG. 9b by $L_2$, and in FIG. 9c by $L_3$.

Figure 7:
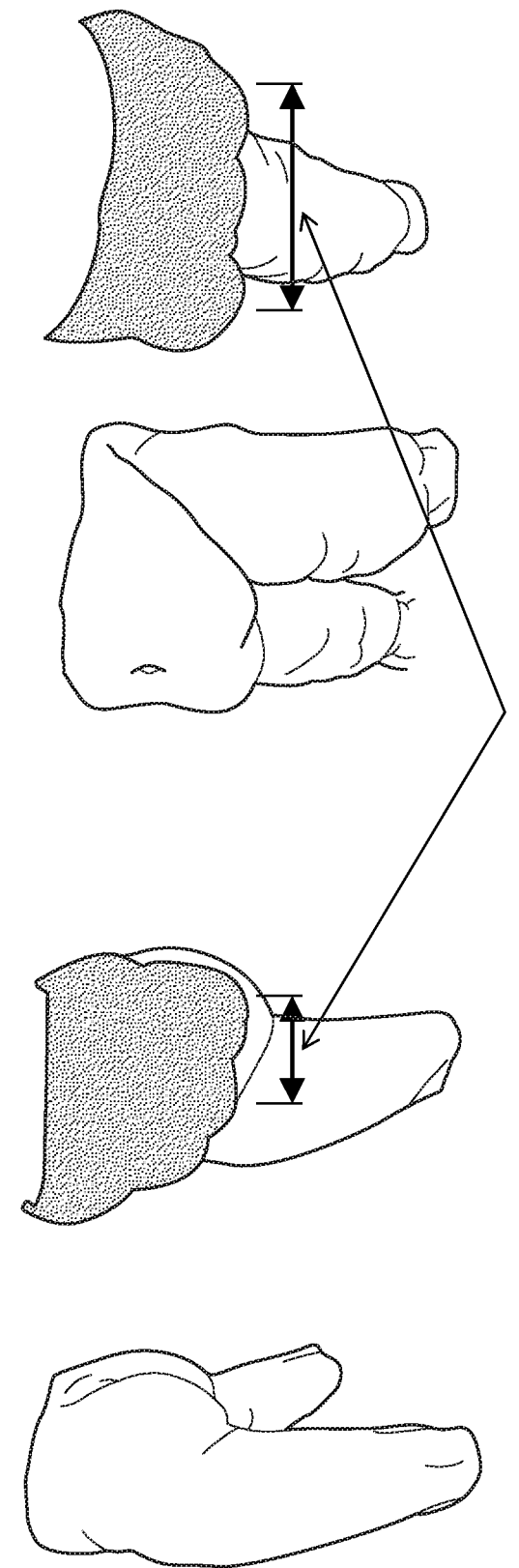
FIG. 7 shows representative female body shapes of differing BMI and the "Flat Region Through the Crotch."

"Flat Region Through Crotch" is the approximated longitudinally flat region, parallel to the sagittal plane, through the crotch. This is illustrated in FIG. 7.

"Hip" means the circumference of the body at the level of the maximum posterior protuberance of buttocks.

"Waist" means the horizontal circumference of the waist at the level of the center of the navel (omphalion).

"Thigh" means the circumference of the thigh at its juncture with the buttock, the measurement made perpendicular to the long axis of the thigh.

"Target Waist" means for a product with a recommended waist range, the midpoint of that recommended waist range.

"Target Hip" means for a product with a recommended hip range, the midpoint of that recommended hip range.

"Target Weight" means for a product with a recommended weight range, the midpoint of that recommended weight range.

"Target Thigh" means for a product with a recommended thigh range, the midpoint of that recommended thigh range.

Figure 13:
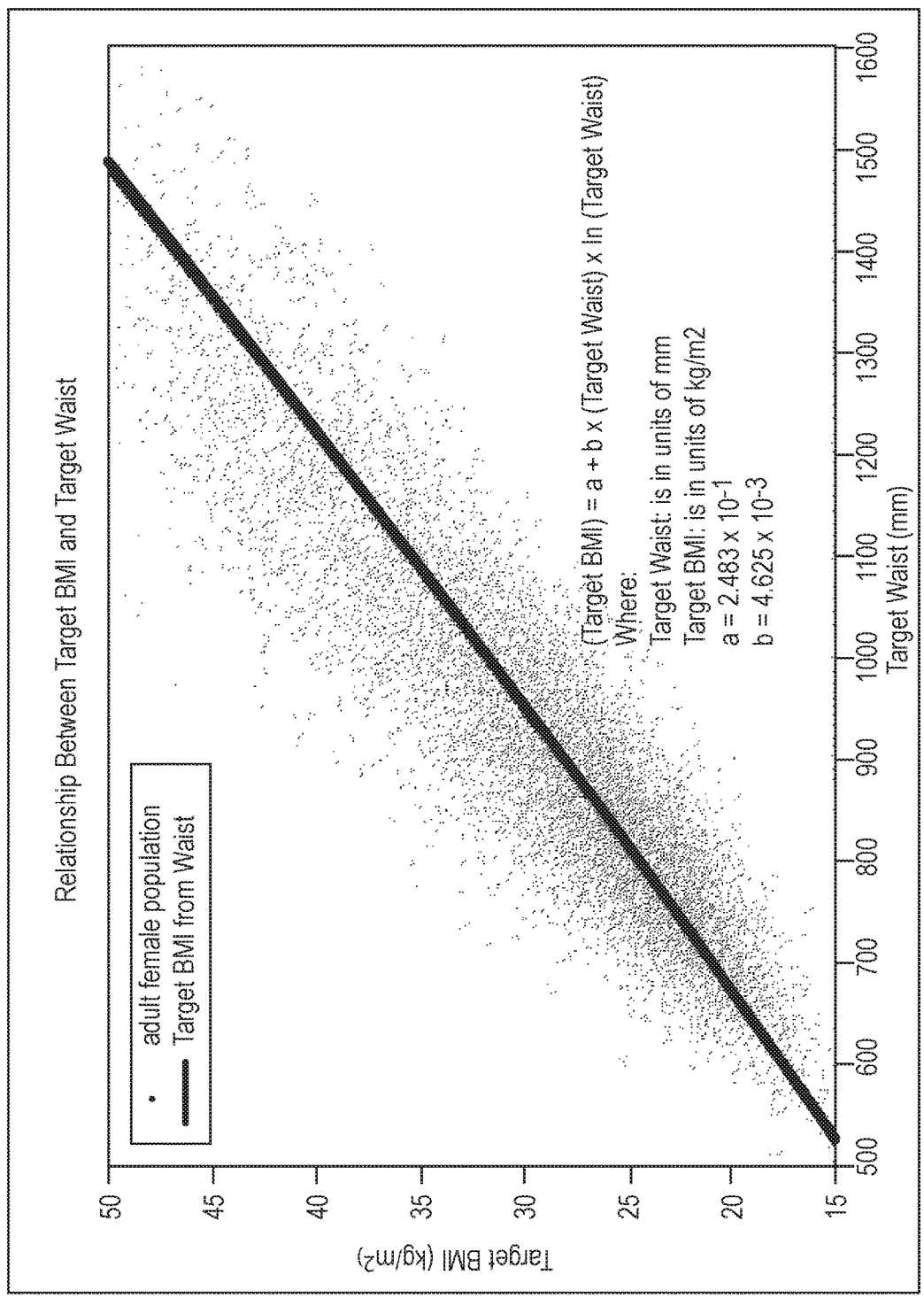
FIG. 13 is a chart showing the relationship between Target BMI and Target Waist.

"Target BMI from Waist" is determined from the Target Waist and is shown in FIG. 13. It is calculated by:

$$(\text{Target BMI from Waist}) = a + b \times (\text{Target Waist}) \times \ln(\text{Target Waist})$$

Figure 14:
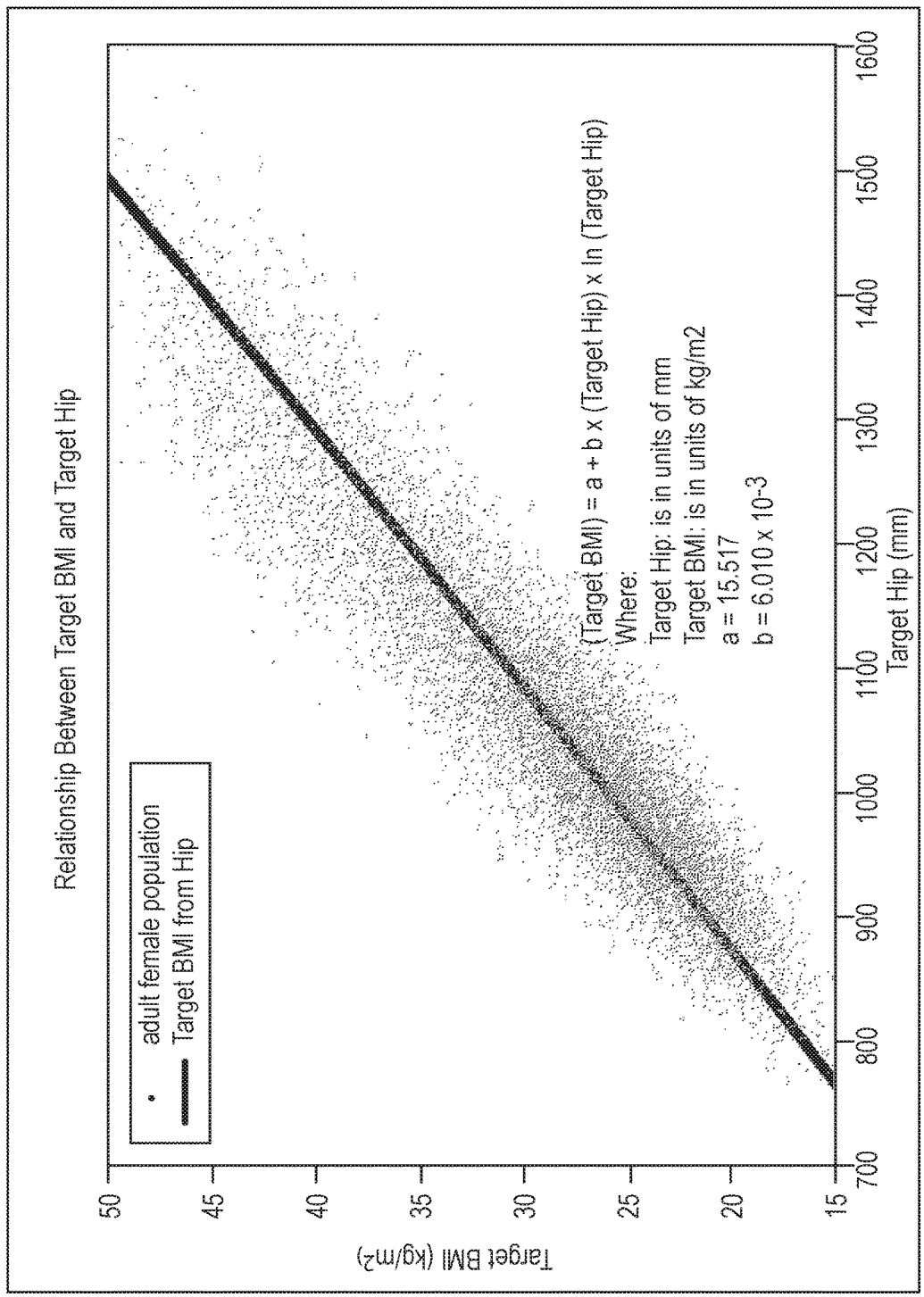
FIG. 14 is a chart showing the relationship between Target BMI and Target Hip.

Where:
Target Waist: is in units of mm
Target BMI: is in units of kg/m²
$a = -2.483 \times 10^{-1}$
$b = 4.625 \times 10^{-3}$ "Target BMI from Hip" is determined from the Target Hip and is shown in FIG. 14. It is calculated by:

$$(\text{Target BMI from Hip}) = a + b \times (\text{Target Hip}) \times \ln(\text{Target Hip})$$

Figure 12:
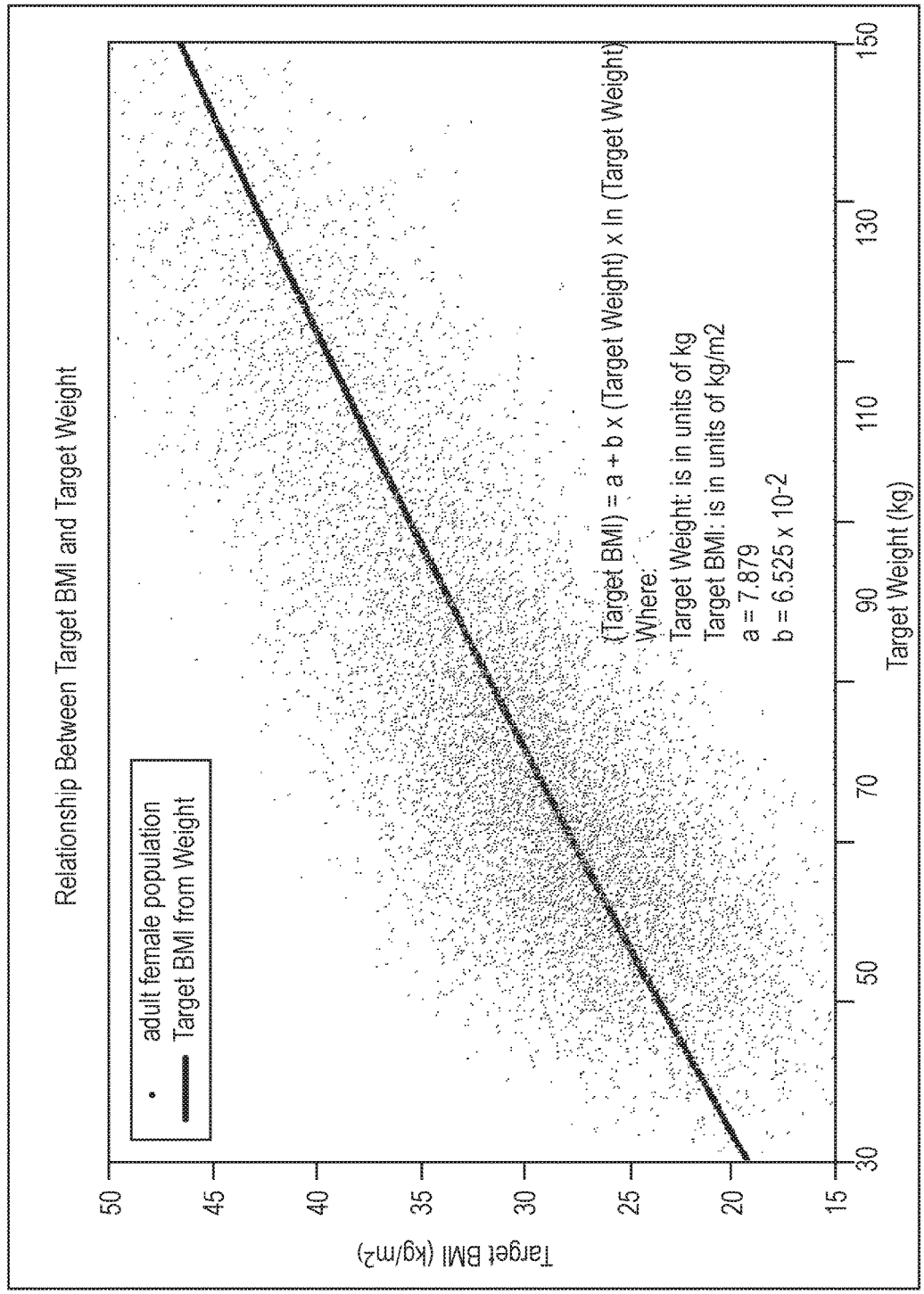
FIG. 12 is a chart showing the relationship between Target BMI and Target Weight.

Where:
Target Hip: is in units of mm
Target BMI: is in units of kg/m²
$a = -15.517$
$b = 6.010 \times 10^{-3}$ "Target BMI from Weight" is determined from the Target Weight and is shown in FIG. 12. It is calculated by:

$$(\text{Target BMI from Weight}) = a + b \times (\text{Target Weight}) \times \ln(\text{Target Weight})$$

Figure 15:
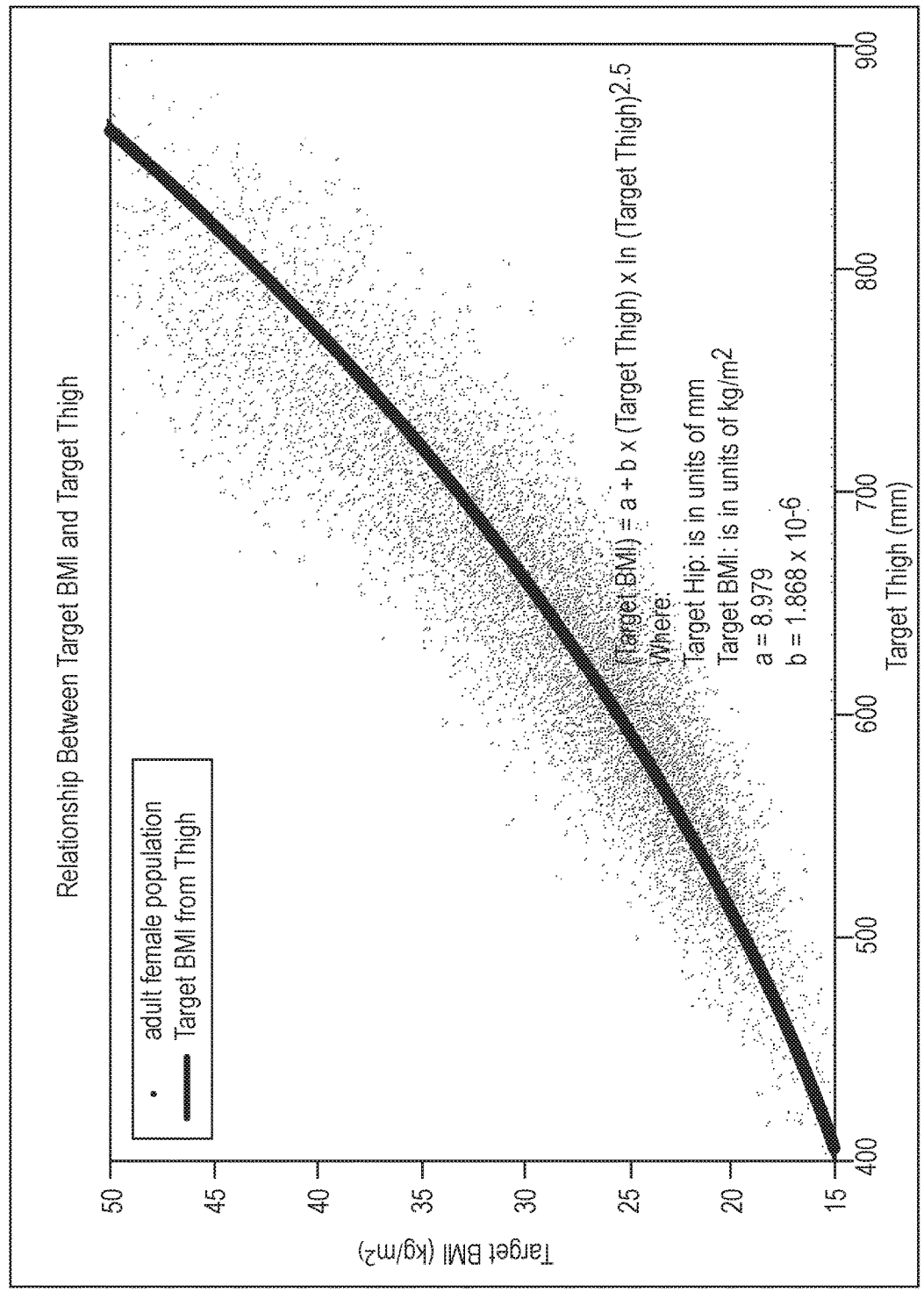
FIG. 15 is a chart showing the relationship between Target BMI and Target Thigh.

Where:
Target Weight: is in units of kg
Target BMI: is in units of kg/m²
$a = 7.879$
$b = 6.525 \times 10^{-2}$ "Target BMI from Thigh" is determined from the Target Thigh and is shown in FIG. 15. It is calculated by:

$$(\text{Target BMI from Thigh}) = a + b \times (\text{Target Thigh}) \times (\text{Target Thigh})^{2.5}$$

Where:
Target Thigh: is in units of mm
Target BMI: is in units of kg/m²
$a = 8.979$
$b = 1.868 \times 10^{-6}$ "Target BMI" means the Target BMI from Waist if a waist range is recommended. If a waist range is not recommended then the Target BMI means the Target BMI from Hip if a hip range is recommended. If neither a hip range nor a waist range is recommended, then Target BMI means the Target BMI from Weight if a weight range is recommended. If neither a waist, hip nor weight range is recommended, then Target BMI means the Target BMI determined from a panty size if a panty size is recommended. If a panty size is not recommended, then the Target BMI is determined from the clothing size if a clothing size is recommended. See FIGS. 26-30 1-5 for examples.

FIG. 26 shows an example of how the Target BMI is determined for absorbent articles where a waist range and a weight range are recommended.

FIGS. 27 and 28 show examples of how the Target BMI is determined for absorbent articles where a waist range, a hip range and a weight range are recommended.

Figure 29:
FIG. 29 is a table illustrating how the Target BMI is determined for parity and clothing sizes where a waist range and a hip range are recommended.
Figure 30:
FIG. 30 is a table illustrating how the Target BMI is determined for panty and clothing sizes where a waist range and a hip range are recommended.

FIGS. 29 and 30 show examples of how the Target BMI is determined for panty and clothing sizes where a waist range and a hip range are recommended.

Consumers who are urinary incontinent often are traumatized by the condition. Many aspects of the condition contribute to the trauma, like the fear of having an incontinent event in public. Even when wearing an absorbent article, there is still the fear of leaking, and the fear of her absorbent article being noticeable under her clothes. As such providing a product experience that helps normalize the condition by providing a more underwear-like, thin and body conforming structure across the entire BMI range is one of the objects of the present disclosure.

The body mass index (BMI) is a classification system for body shapes based upon height and mass. BMI may be calculated as follows:

$$BMI = \frac{\text{weight(kg)}}{\text{height(m)}^2} = \frac{703 * \text{weight(lb)}}{\text{height(in)}^2}$$

The BMI comprises different classes of body mass, including: underweight (BMI<20), normal weight (BMI 20-25), overweight (BMI 25-30), obese (BMI 30-40), and morbidly obese (BMI>40).

Figure 16:
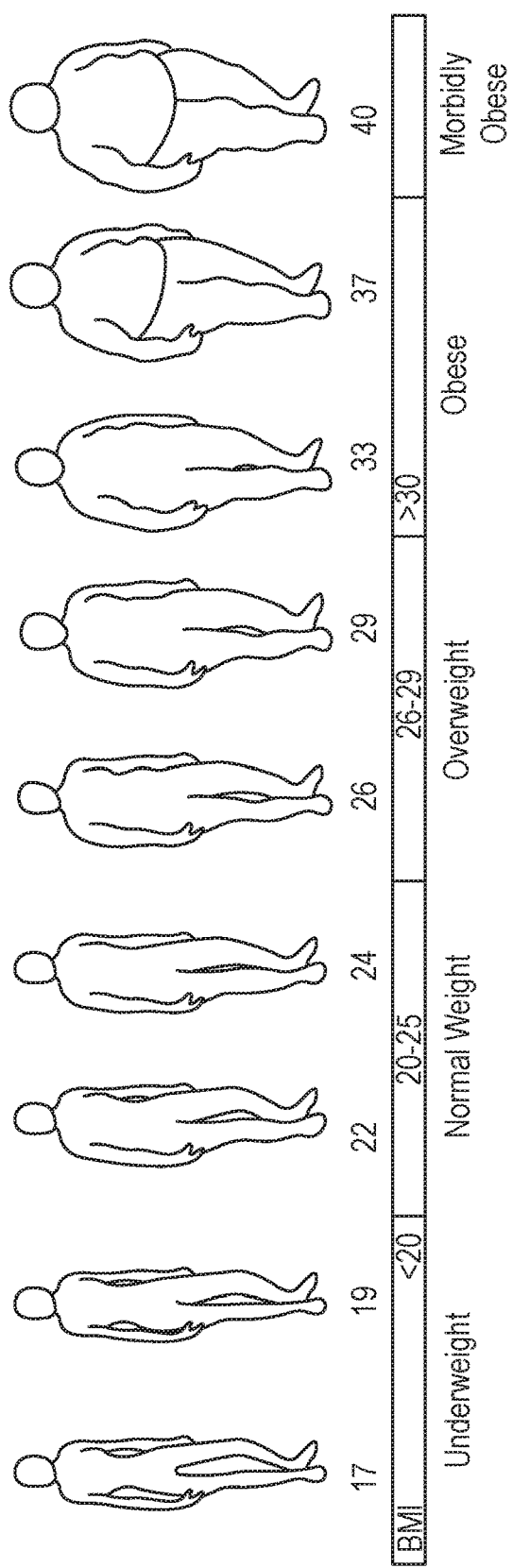
FIG. 16 shows how the general female body shape changes as BMI increases.
Figure 17:
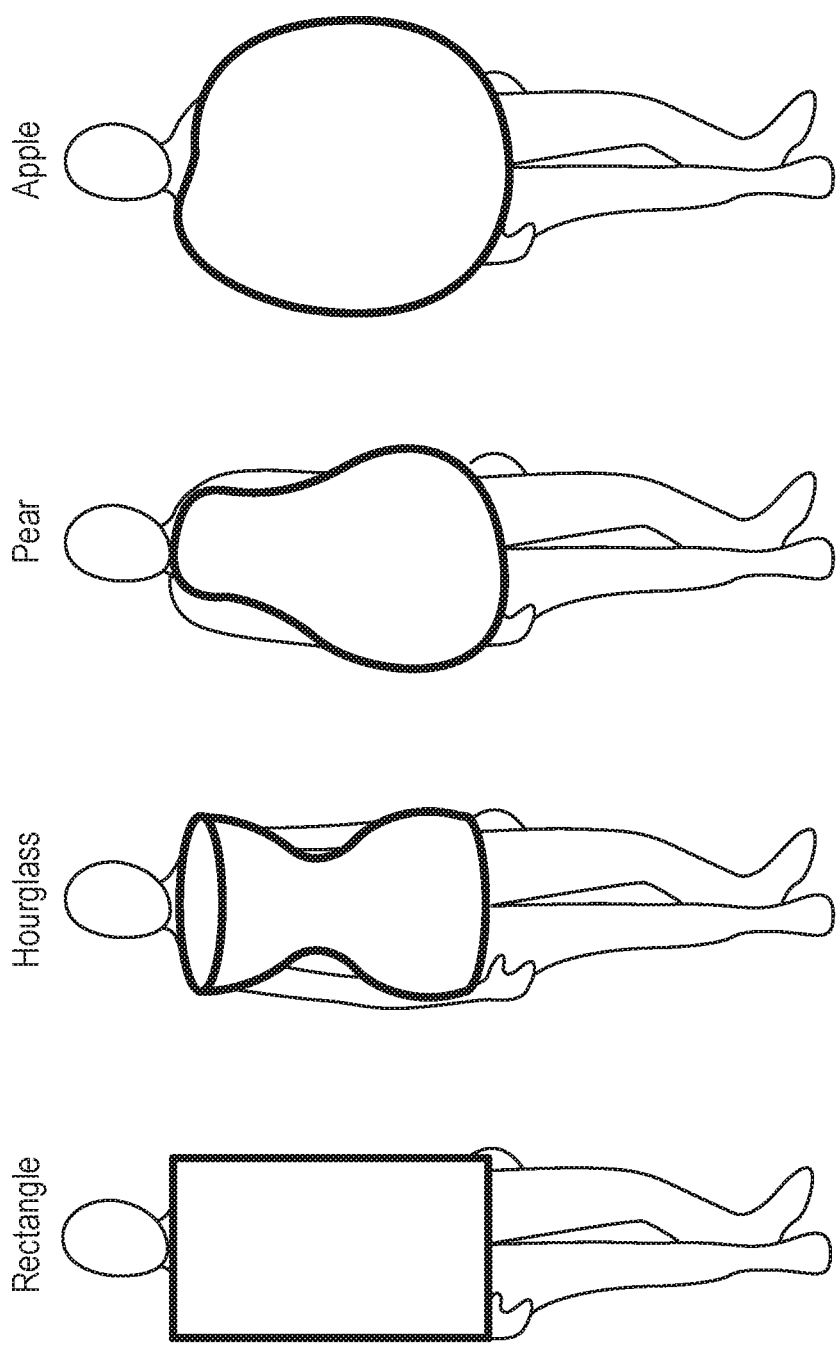
FIG. 17 depicts the variability of female body shapes within each BMI class.

FIG. 16 illustrates how the general female body shape changes as BMI increases. FIG. 17 illustrates a variety of specific shapes that may exist within each BMI class: rectangle (also known as cylindrical), hourglass, pear, and apple. The higher her BMI, the further to the right (toward the apple) a woman typically is on this body shape scale. The prevalence of these shapes differs across the BMI range, for instance, higher BMI women have a higher probability of being apple or pear shaped. Adult absorbent articles may be marketed to women of a particular body shape, such as apple, rather than focusing on exact BMI values (which may be off-putting to a consumer), in order to match a wearer with the article that may best fit her unique body shape or size.

Figure 4:
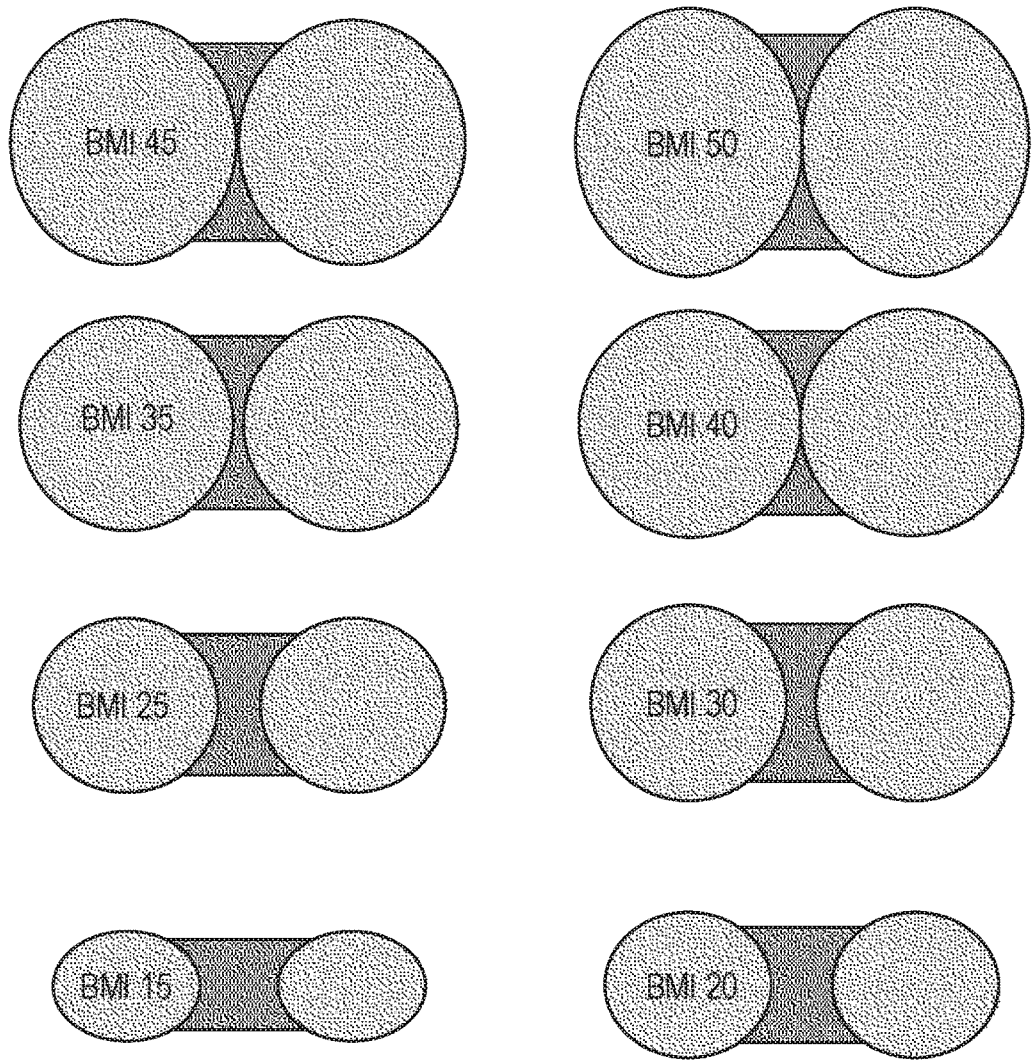
FIG. 4 shows the average female morphological shapes at plane B:B of FIG. 2 as a function of BMI.
Figure 5:
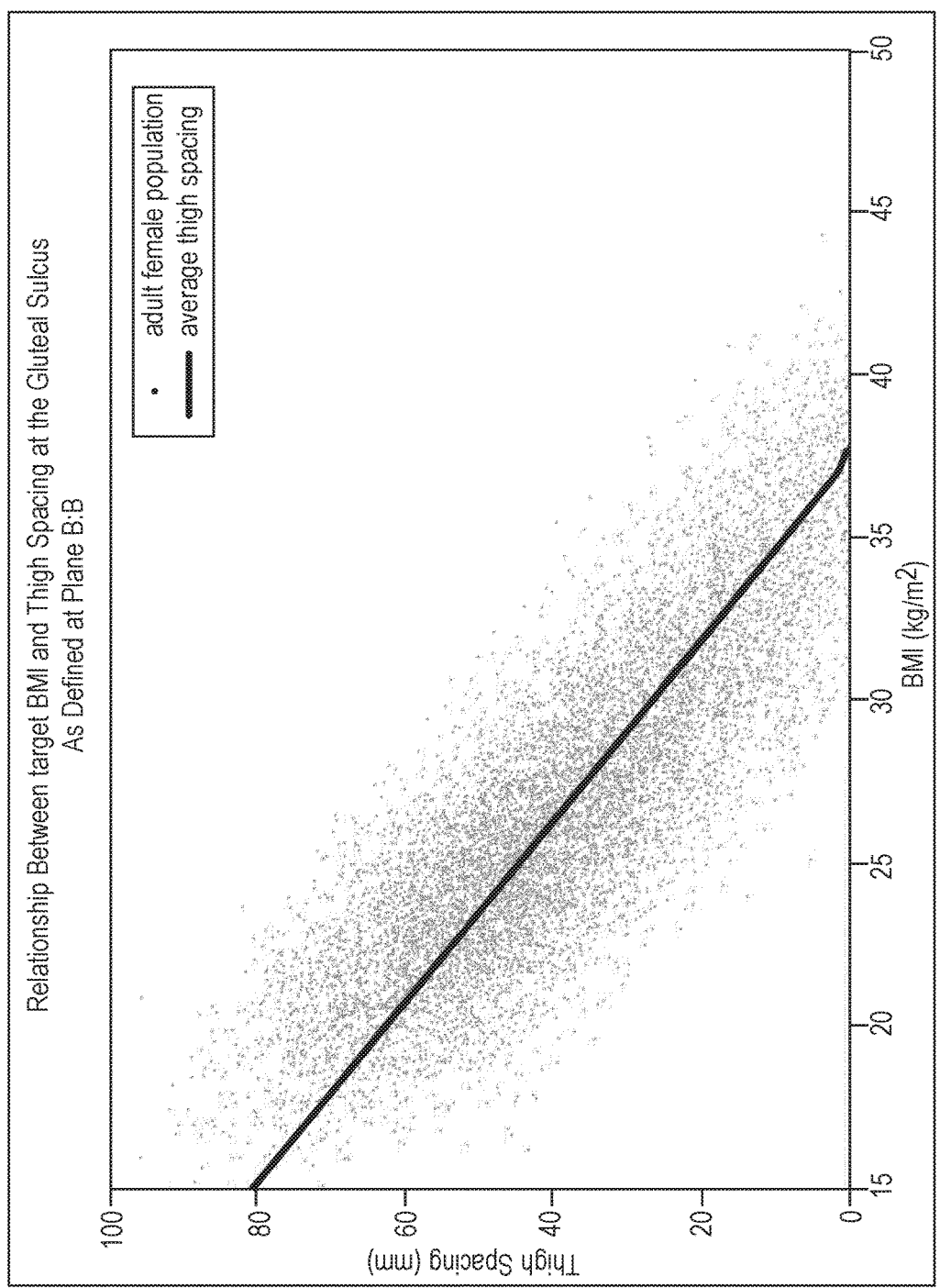
FIG. 5 is a chart showing the relationship between Target BMI and Thigh Spacing at plane B:B of FIG. 2.
Figure 6:
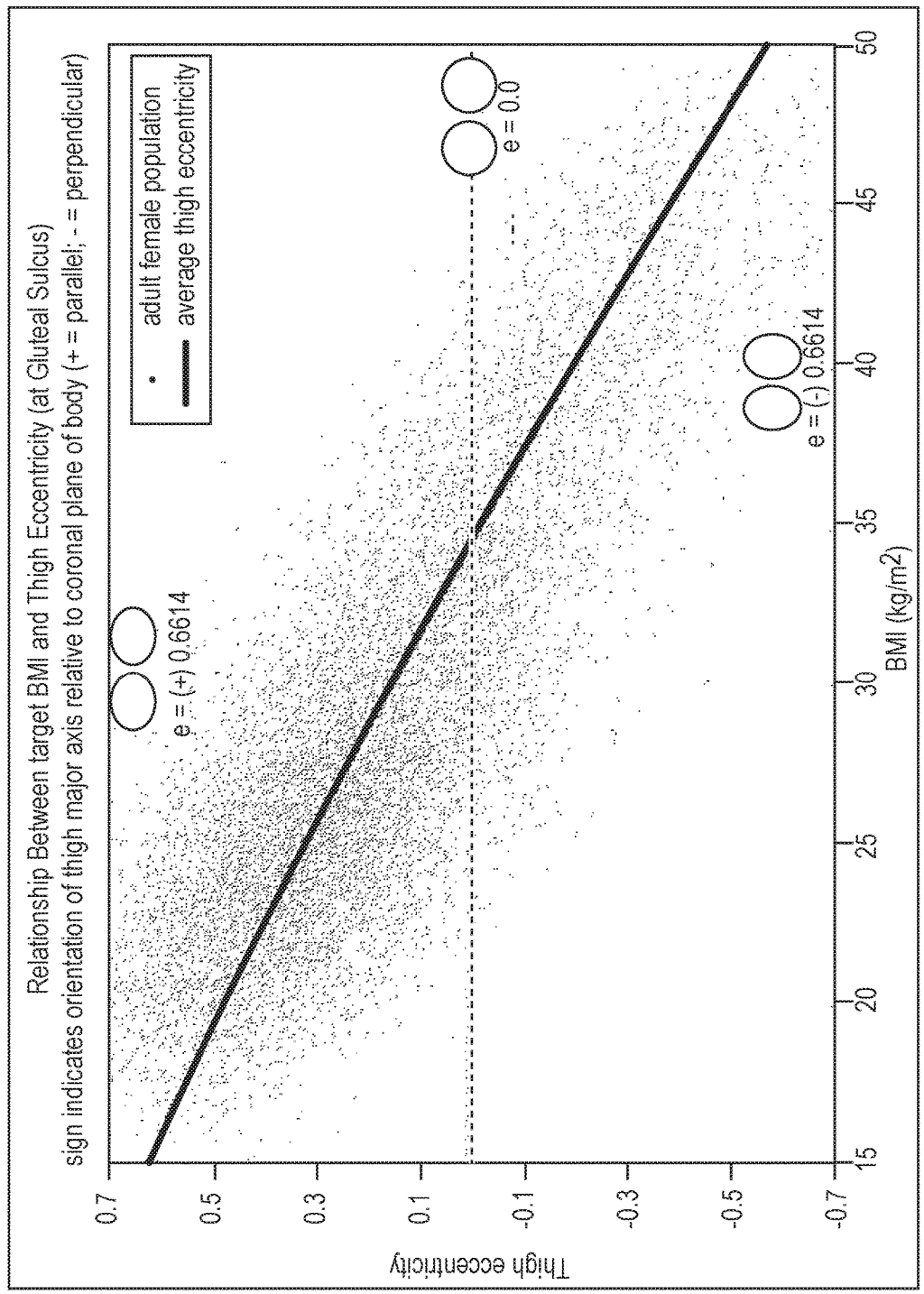
FIG. 6 is a chart showing the relationship between Target BMI and Thigh Eccentricity at plane B:B of FIG. 2.
Figure 8:
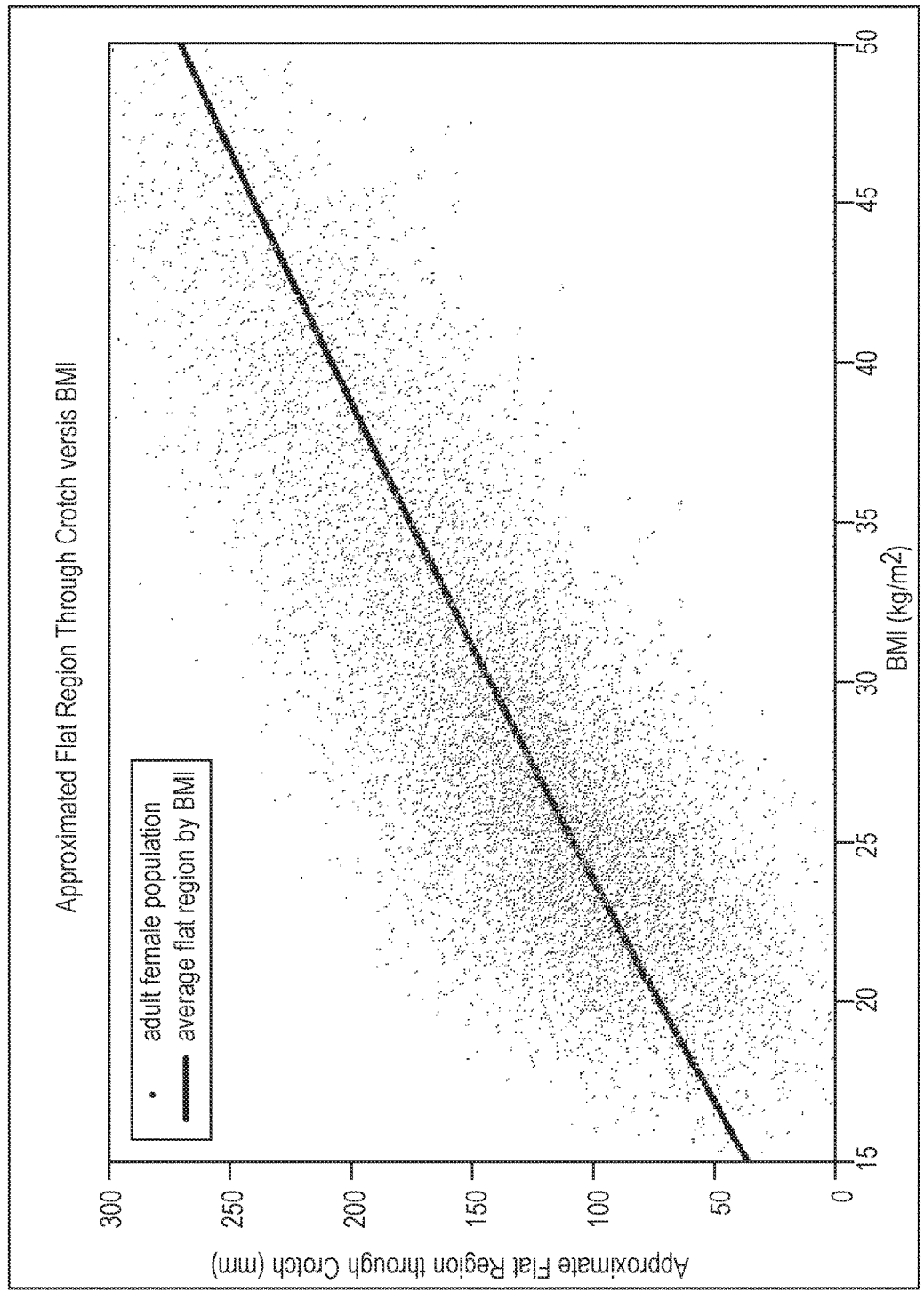
FIG. 8 is a chart showing the relationship between Target BMI and the "Flat Region Through the Crotch."

Some regions where the shape of the female body change as BMI gets higher is in the shape and spacing of the thighs. This is illustrated in FIG. 4, and in the charts on FIG. 5 and on FIG. 6. As BMI increases, the spacing between the thighs at the Gluteal Sulcus decreases. Additionally, as BMI gets higher, the eccentricity of the thigh at the Gluteal Sulcus changes as is illustrated in FIG. 4. This change results in a larger radius (smaller curvature) and a longer thigh axis (perpendicular to the coronal plane of the body). Additionally, as BMI increases the length of the Flat Region Through Crotch (parallel to the sagittal plane) increases as is illustrated in FIG. 7 and by the chart on FIG. 8.

It may be desirable to link the shape and spacing of core channels to these physical body dimensions in order to achieve a better fitting, better conforming article. This may increase the wearing comfort for each consumer while reducing leakage.

Table 6 below illustrates an example of an inventive array of 3 packages, as illustrated in FIGS. 10a-c, whose channel shapes better match the body shapes of the Target BMI's of the consumers each package is intended to fit and thereby providing better fit and comfort while reducing the chance of leakage.

TABLE 6

Example of Inventive Product Array

| 1st Inventive Array (3 package array) | Average Targeted BMI | Channel Length (mm) | Channel Spacing (mm) | Channel Curvature (1/m) | Channel Arm Angle (deg) |
|---|---|---|---|---|---|
| 1st Package in Array | 27 | 300 | 45 | 11.1 | n/a |
| 2nd Package in Array | 35 | 370 | 10 | 8.3 | n/a |
| 3rd Package in Array | 45 | 420 | 0 | 6.7 | n/a |

Figure 11C:
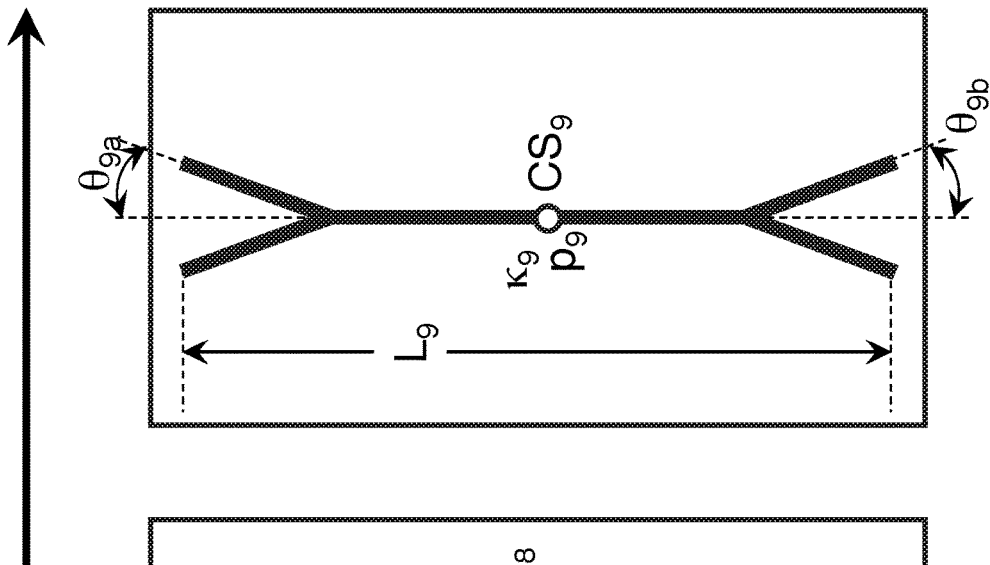
FIG. 11a-c show examples of different core channel configurations for consumers of differing BMI's.
Figure 11B:
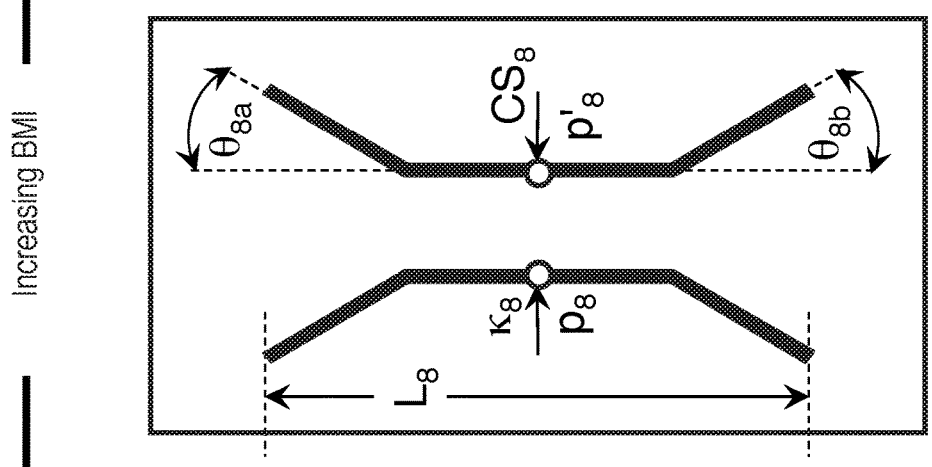
Figure 11A:
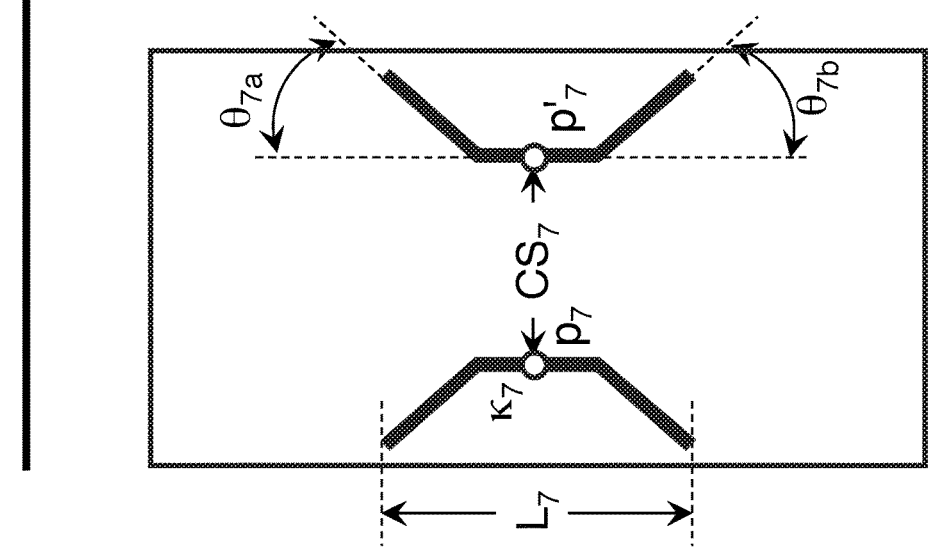

Table 7 below illustrates an example of an inventive array of 3 packages, as illustrated in FIGS. 11a-c, whose channel shapes better match the body shapes of the Target BMI's of the consumers each package is intended to fit and thereby providing better fit and comfort while reducing the chance of leakage.

TABLE 7

Example of Inventive Product Array

| 2nd Inventive Array (3 package array) | Average Targeted BMI | Channl Length (mm) | Channel Spacing (mm) | Channel Curvature (1/m) | Channel Arm Angle (deg) |
|---|---|---|---|---|---|
| 1st Package in Array | 27 | 300 | 45 | 0 | 40° |
| 2nd Package in Array | 35 | 370 | 10 | 0 | 30° |
| 3rd Package in Array | 45 | 420 | 0 | 0 | 20° |

These inventive arrays are provided simply as non-limiting examples. Other inventive arrays are possible within the scope of this disclosure.

Absorbent Article

The absorbent articles of the present disclosure are generally designed and configured to manage bodily exudates such as urine, menses, feces or other vaginal discharges.

In one embodiment, an absorbent article may comprise a chassis comprising a topsheet, a backsheet, and an absorbent core disposed at least partially between the topsheet and the backsheet. The absorbent chassis may comprise a waistband, leg cuffs and or elastic strands. In various embodiments, referring to FIG. 1, an example absorbent article 10 is shown in its flat uncontracted state prior to joining the waist regions to complete the waist opening by for example fastening components 53a and b (illustrated in FIG. 22).

Figure 1:
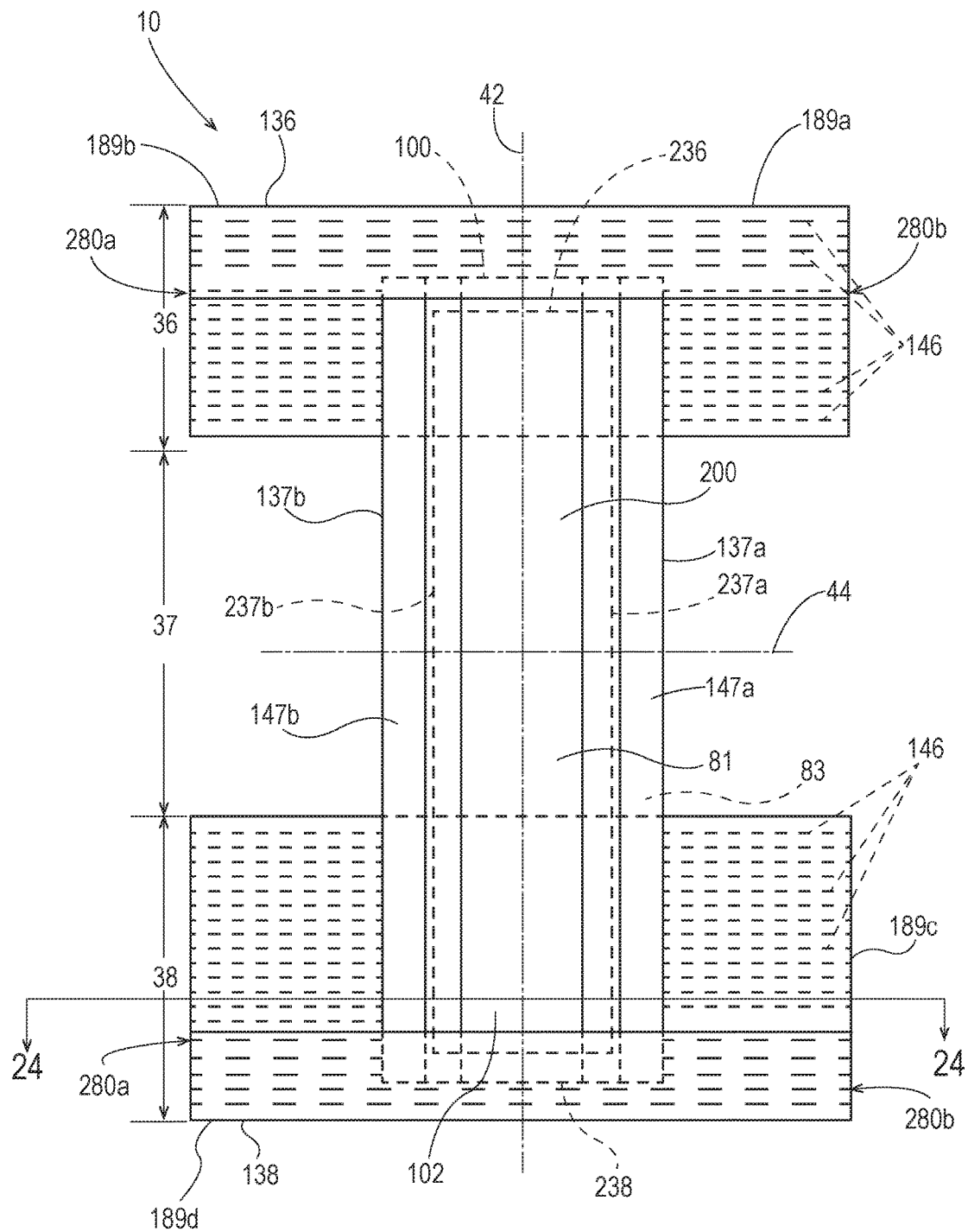
FIG. 1 is a plan view of a pant diaper with a continuous belt in the front and back waist regions.

In one embodiment, referring to FIG. 1, one end portion of the absorbent article 10 may be configured as a front waist region 36 and the longitudinally opposing end portion may be configured as a back waist region 38. An intermediate portion of the absorbent article 10 extending longitudinally between the front waist region 36 and the back waist region 38 may be configured as a crotch region 37. In one embodiment, although not illustrated as such, the length of each of the front waist region 36, the back waist region 38 and the crotch region 37 may be about ⅓ of the length of the absorbent article 10, for example. In other embodiments, the length of each of the front waist region 36, the back waist region 38, and the crotch region 37 may have other dimensions. In various embodiments, the absorbent article 10 may have a laterally extending front waist end edge 136 in the front waist region 36 and a longitudinally opposing and laterally extending back waist end edge 138 in the back waist region 38.

In one embodiment, referring to FIG. 1, a chassis 100 of the absorbent article 10 may comprise a first longitudinally extending side edge 137a and a laterally opposing and second longitudinally extending side edge 137b. Both of the side edges 137 may extend longitudinally between the front waist end edge 136 and the back waist end edge 138. The chassis 100 may form a portion of the laterally extending front waist end edge 136 in the front waist region 36 and a portion of the longitudinally opposing and laterally extending back waist end edge 138 in the back waist region 38. Furthermore, the chassis 100 may comprise an interior surface 102, an exterior surface 104, a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 137a and through a midpoint of the second side edge 137b.

In various embodiments, a portion of or the whole absorbent article 10 may be made to be laterally extensible. The extensibility of the absorbent article 10 may be desirable in order to allow the absorbent article 10 to conform to a body of a wearer during movement by the wearer. The extensibility may also be desirable, for example, in order to allow the caregiver to extend the front waist region 36, the back waist region 38, the crotch region 37, and/or the chassis 100 to provide additional body coverage for wearers of differing size, i.e., to tailor the absorbent article 10 to the individual wearer. Such extension may provide the absorbent article 10 with a generally hourglass shape, so long as the crotch region 37 is extended to a relatively lesser degree than the waist regions 36 and/or 38. This extension may also impart a tailored appearance to the absorbent article 10 during use.

Any or all portions of the absorbent article may comprise a bacteriophage composition as described in U.S. Ser. No. 61/931,229, titled DISPOSABLE ABSORBENT ARTICLES COMPRISING BACTERIOPHAGES AND RELATED METHODS, and filed on Jan. 24, 2014.

Topsheet

Figure 24:
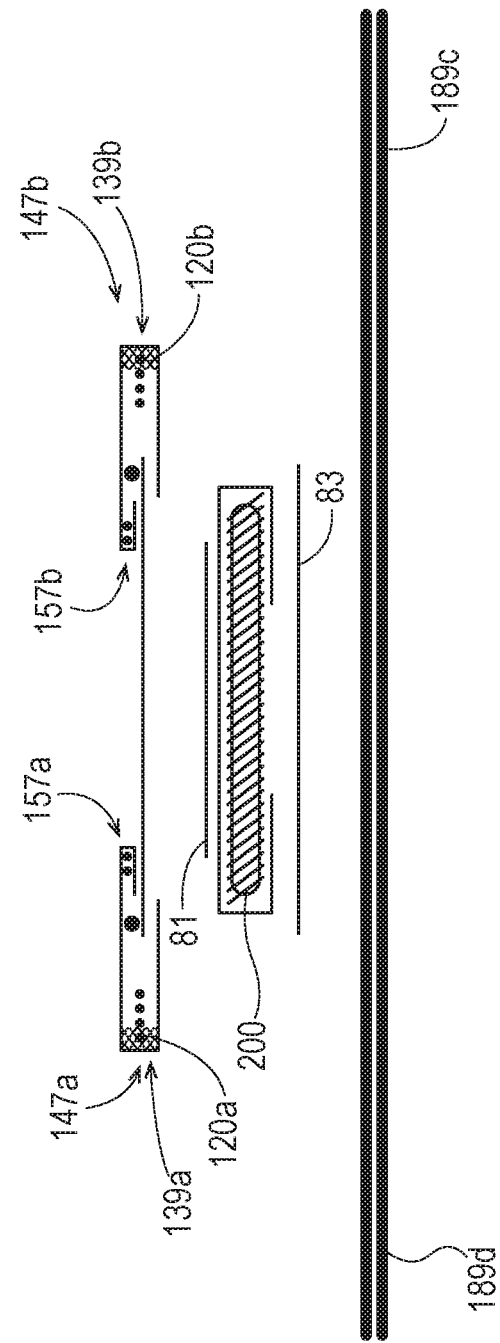
FIG. 24 is a schematic cross section view of a back belt-like flap suitable in one embodiment of the disclosure, taken along line 24-24 of FIG. 1.

In one embodiment, referring to FIGS. 1 and 24, the absorbent article 10 may comprise a topsheet 81. The topsheet 81 may be compliant, soft feeling, and non-irritating to the wearer's skin and may be elastically stretchable in one or more directions. Further, the topsheet 81 may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis 100 when these fluids are expelled from the body. A suitable topsheet 81 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324, 246, 4,342,314, 4,463,045, 5,006,394, 5,628,097, 5,916,661, 6,545,197, and 6,107,539.

Apertured film or nonwoven topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 81 comprises fibers, the fibers may be spunbond, carded, wet-laid, meltblown, hydroentangled, or otherwise processed, for example, as is generally known in the art.

The topsheet may comprise a skin care lotion. Examples of suitable lotions include, but are not limited to, those described in U.S. Pat. Nos. 5,607,760; 5,609,587; 5,635, 191; 5,643,588; and 5,968,025, and as described in U.S. Application No. 61/391,353, and as described in U.S. Pub. No. 2014-0257216. Beyond these compositions, the absorbent article may comprise soluble cyclodextrin derivatives such as those described in U.S. Pub. No. 2014/0274870.

Additionally, the topsheet of the present disclosure may be a tufted laminate web as disclosed in U.S. Pat. No. 7,410,683, and/or may be an apertured web as disclosed in PCT/CN2014/083769 having an international filing date of Aug. 6, 2014.

In one embodiment, the topsheet may comprise graphics (e.g., 116 in FIG. 20) such that depth perception is created as described in U.S. Pat. No. 7,163,528.

Backsheet

Figure 23:
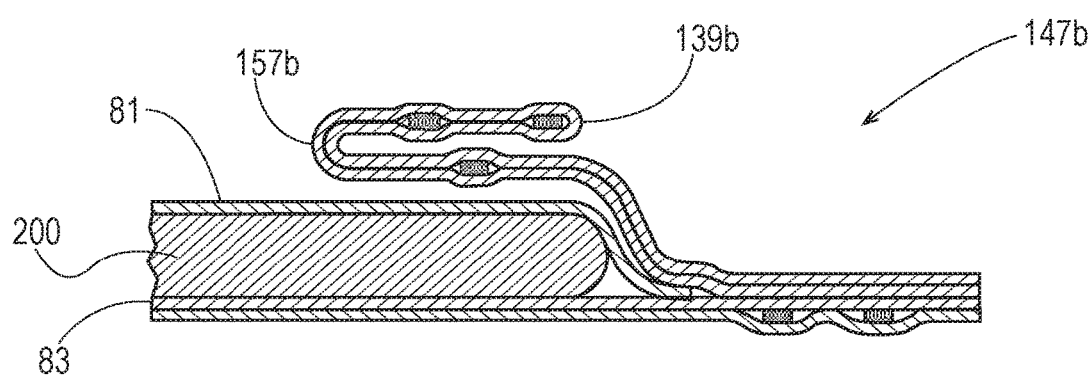
FIG. 23 is a schematic cross section view taken along line 23-23 in FIG. 18 of an example of a folded outer leg cuff suitable in one embodiment of the disclosure.

In one embodiment, referring to FIGS. 23 and 24, for example, the absorbent article 10 may comprise a backsheet 83. The backsheet 83 may be impervious, or at least partially impervious, to fluids or body exudates (e.g., menses, urine, and/or runny feces) and may be manufactured from a thin plastic film, although other flexible liquid impervious materials may also be used. The backsheet 83 may prevent the body exudates or fluids absorbed and contained in an absorbent core of the absorbent article 10 from wetting articles which contact the absorbent article 10, such as bedsheets, pajamas, clothes, and/or undergarments. The backsheet 83 may comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

In one embodiment, the backsheet 83 may be embossed and/or matte-finished to provide a more cloth-like appearance. Further, the backsheet 83 may permit vapors to escape from the absorbent core of the absorbent article 10 (i.e., the backsheet 83 is breathable) while still preventing, or at least inhibiting, fluids or body exudates from passing through the backsheet 83. In one embodiment, the size of the backsheet 83 may be dictated by the size of the absorbent article 10 and the design or configuration of the absorbent article 10 to be formed, for example.

Absorbent Core

In various embodiments, referring to FIGS. 23 and 24, the absorbent article 10 may comprise an absorbent core (also referred to as an "absorbent member" or "absorbent assembly" or "absorbent structure" or "absorbent composite") 200 that is disposed between the topsheet 81 and the backsheet 83. The absorbent core 200 may comprise a laterally extending front edge 236 in the front waist region 36, a longitudinally opposing and laterally extending back edge 238 in the back waist region 38, a first longitudinally extending side edge 237a, and a laterally opposing and second longitudinally extending side edge 237b. Both of the side edges 237 may extend longitudinally between the front edge 236 and the back edge 238. In one embodiment, more than one absorbent core 200 or more than one absorbent core layer may be provided in an absorbent article 10, for example. The absorbent core 200 may be any suitable size or shape that is compatible with the absorbent article 10. Example absorbent structures for use as the absorbent core 200 of the present disclosure that have achieved acceptance and commercial success are described in U.S. Pat. Nos. 4,610,678; 4,673,402; 4,888,231; and 4,834,735.

In one embodiment, suitable absorbent cores may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100% as determined by weight. Furthermore, a portion of the absorbent core may comprise a microfiber glue (if applicable). Such absorbent cores, microfiber glues, and absorbent gelling materials are described in U.S. Pat. Nos. 5,599,335; 5,562,646; 5,669,894; 6,790,798; and 7,521,587 and in U.S. Pat. Publ. No. 2004/0158212.

In one embodiment, the core, including multiple layers making up the core system, may be printed and embossed as described in U.S. Pat. No. 8,536,401.

In one embodiment, the core may be separable from the chassis as disclosed in U.S. Pat. Nos. 6,989,006; 7,381,202; 7,175,613; 7,824,386; 7,766,887; and 6,989,005. In such embodiments, the measurements described in this disclosure may be made to the chassis alone or may be made to the chassis in combination with the separable core/absorbent assembly.

In one embodiment, the absorbent article of the present disclosure, and particularly, a portion where the absorbent member is disposed, may have a body fluid absorption rate greater than 3 g/sec according to U.S. Pat. No. 6,649,810. According to U.S. Pat. No. 6,649,810, the expression "the portion (of the absorbent article) where the absorbent member is disposed" is intended to mean the portion occupied by the absorbent member when the absorbent article is flatly unfolded and seen in its plan view.

In one embodiment, the absorbent structure may have an intake factor greater than 3 according to U.S. Pat. No. 7,073,373, wherein the intake factor is defined as the absorbent core permeability divided by the normalized retention capacity (which is defined by the Retention Capacity Test—also according to U.S. Pat. No. 7,073,373).

In one embodiment, the absorbent composite has a body fluid absorption greater than 75 g/100 cm2, according to U.S. Pat. No. 6,649,810.

In one embodiment, a target location of the absorbent article may have a wicking value greater than 36%, according to U.S. Pat. No. 6,383,960.

In one embodiment, the absorbent article may have a bending stiffness between 0.05-1.0 gf, according to U.S. Pat. No. 5,810,796.

In one embodiment, the absorbent article may have a crotch fluid absorption rate greater than 3 g/sec according to U.S. Pat. No. 6,649,810. In one embodiment, a freeze-dried composite of the absorbent composite may have an intake rate of at least about 1.9 cubic centimeters (cc) of liquid/second at 80% composite saturation according to U.S. Pat. No. 6,689,934.

In some embodiments the absorbent core 200 may comprise channels as described in U.S. Pat. No. 8,568,566; U.S. Pub. Nos. 2012/316046, 2014/027066, 2014/163500, 2014/163506, 2014/163511, 2012/316526, 2012/316527, 2012/316528, 2012/316529, 2012/316523, 2014/163501, 2014/163502, 2014/163503 and European Pub. Nos. 2532328, 2532329, 2717823, 2717820, 2717821, 2717822, 2532332, 2740449, and 2740452.

Figure 25:
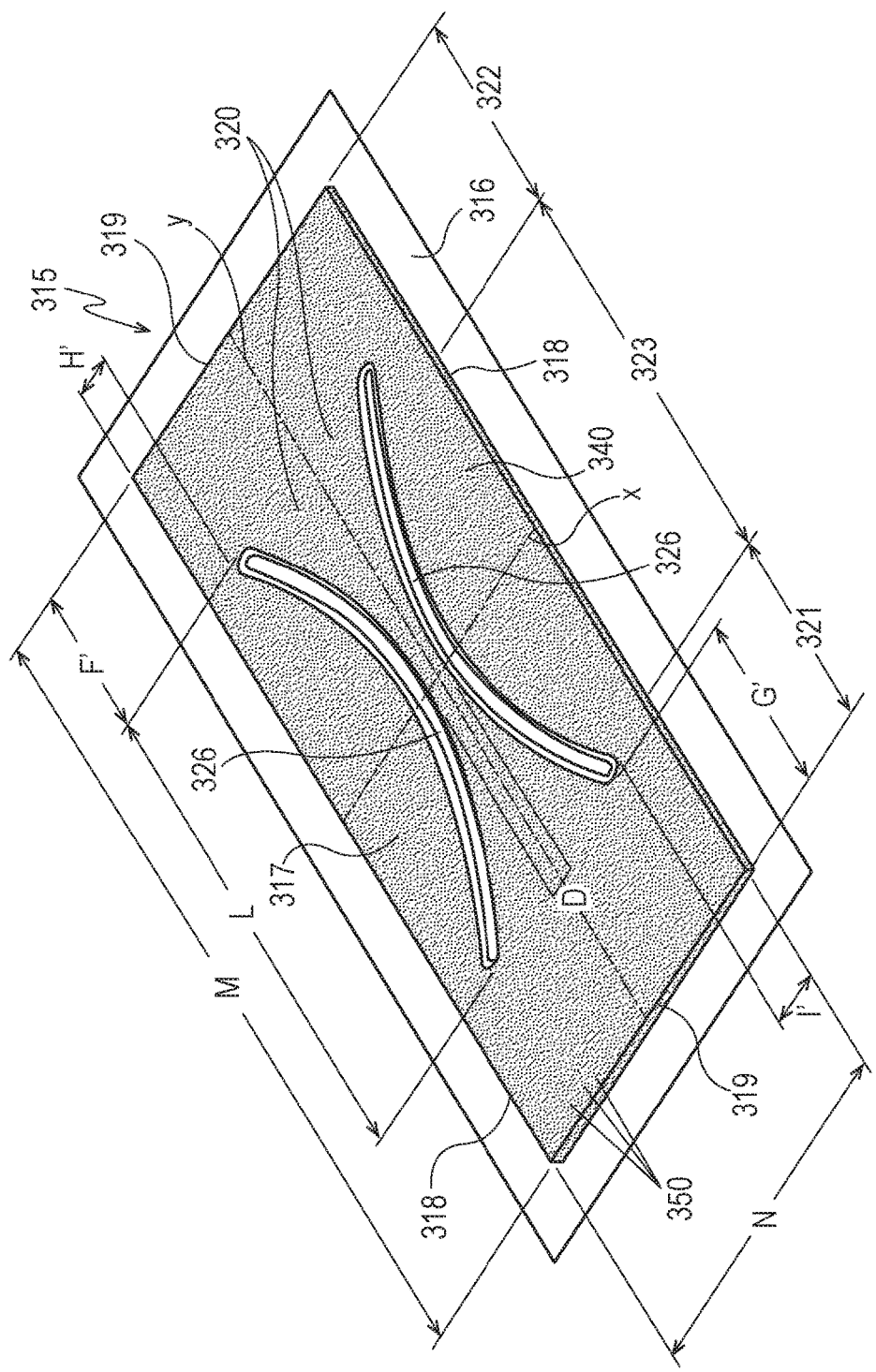
FIG. 25 is a schematic perspective view of an absorbent structure including an absorbent layer with two longitudinal main channels.

As shown in FIG. 25, in some embodiments the absorbent layer 317 may comprise at least two channels 326 substantially free of absorbent polymer particles extending through the thickness of the absorbent layer in the longitudinal dimension of the absorbent layer. By extending in the longitudinal dimension of the absorbent layer, it is meant that the channels extend essentially in the longitudinal dimension, i.e. they extend more in the longitudinal dimension than in the transverse dimension, e.g. at least twice as much in the longitudinal dimension than in the transverse dimension.

"Channels" as used herein refer to discrete portions of one or more of the absorbent layers of the absorbent core extending through the thickness of the absorbent layer which are substantially free of absorbent polymer (particles or fibers), i.e., no absorbent polymer particles are intentionally present in such a channel (longitudinal main channel or secondary channel) of an absorbent structure. However, it should be understood that, accidentally, a small, negligible amount of absorbent polymer particles may be present in the channel, which may not contribute to any significant degree to the overall functionality (e.g. absorbency of the absorbent structure). Typically, the channels possess two transverse edges (in the shortest dimension) and two longitudinal edges (in the longest dimension) running between the transverse edges. The transverse edges of the channels may be straight (i.e., perpendicular to the longitudinal side edges), angled or curved. The channels may have an average width w of at least 3 mm (the average of a channel is defined as the average distance between the longitudinal side edges) or may have at least 4% of the width of the absorbent layer.

The channels may be permanent. By permanent, it is meant that the integrity of the channels is at least partially maintained both in dry state and wet state, i.e., the channels are resistant to external forces caused by movements of the diaper's wearer. Permanent channels are obtained by immobilizing the absorbent polymer on the substrate layer, such as by applying a thermoplastic adhesive material over the absorbent layer. The absorbent layer of the present disclosure may comprise in particular permanent channels formed by bonding of a first substrate layer (316) and a second substrate layer (316') through the channels. Typically, glue may be used to bond both substrate layers through the channel, but it is possible to bond via other known means, for example ultrasonic bonding, pressure bonding or thermal bonding. The supporting layers can be continuously bonded or intermittently bonded within the channels.

Channel Array Embodiments

A first article may have a first channel having a channel spacing from about 0 mm to about 100 mm, from about 10 mm to about 80 mm, or from about 30 mm to about 50 mm. A second article may have a second channel having a channel spacing from about 0 mm to about 100 mm, from about 10 mm to about 80 mm, or from about 30 mm to about 50 mm, wherein the channel spacing of the first channel is greater than the channel spacing of the second channel.

The first channel of the first article may have a channel curvature from about 0/m to about 20/m, from about 5/m to about 15/m, or from about 7/m to about 11/m. The second channel of the second article may have a channel curvature from about 0/m to about 20/m, from about 5/m to about 15/m, or from about 7/m to about 11/m, wherein the channel curvature of the first channel is greater than the channel curvature of the second channel.

The first channel of the first article may have a channel arm angle from about 0° to about 45°, from about 5° to about 30°, or from about 18° to about 23°. The second channel of the second article may have a channel arm angle from about 0° to about 45°, from about 5° to about 30°, or from about 18° to about 23°, wherein the channel arm angle of the first channel is greater than the channel arm angle of the second channel.

The first channel of the first article may have a channel length from about 100 mm to about 500 mm, from about 200 mm to about 400 mm, or from about 250 mm to about 350 mm. The second channel of the second article may have a channel length from about 100 mm to about 500 mm, from about 200 mm to about 400 mm, or from about 250 mm to about 350 mm, wherein the channel length of the first channel is less than the channel length of the second channel.

The first channel may have at least one of a channel spacing, a channel curvature, and a channel arm angle greater than the second channel. The first channel may have at least two of a channel spacing, a channel curvature, and a channel arm angle greater than the second channel. The first channel may have each of a channel spacing, a channel curvature, and a channel arm angle greater than the second channel. In any of these embodiments, the first channel may have a channel length less than the second channel.

Leg Cuffs

Figure 18:
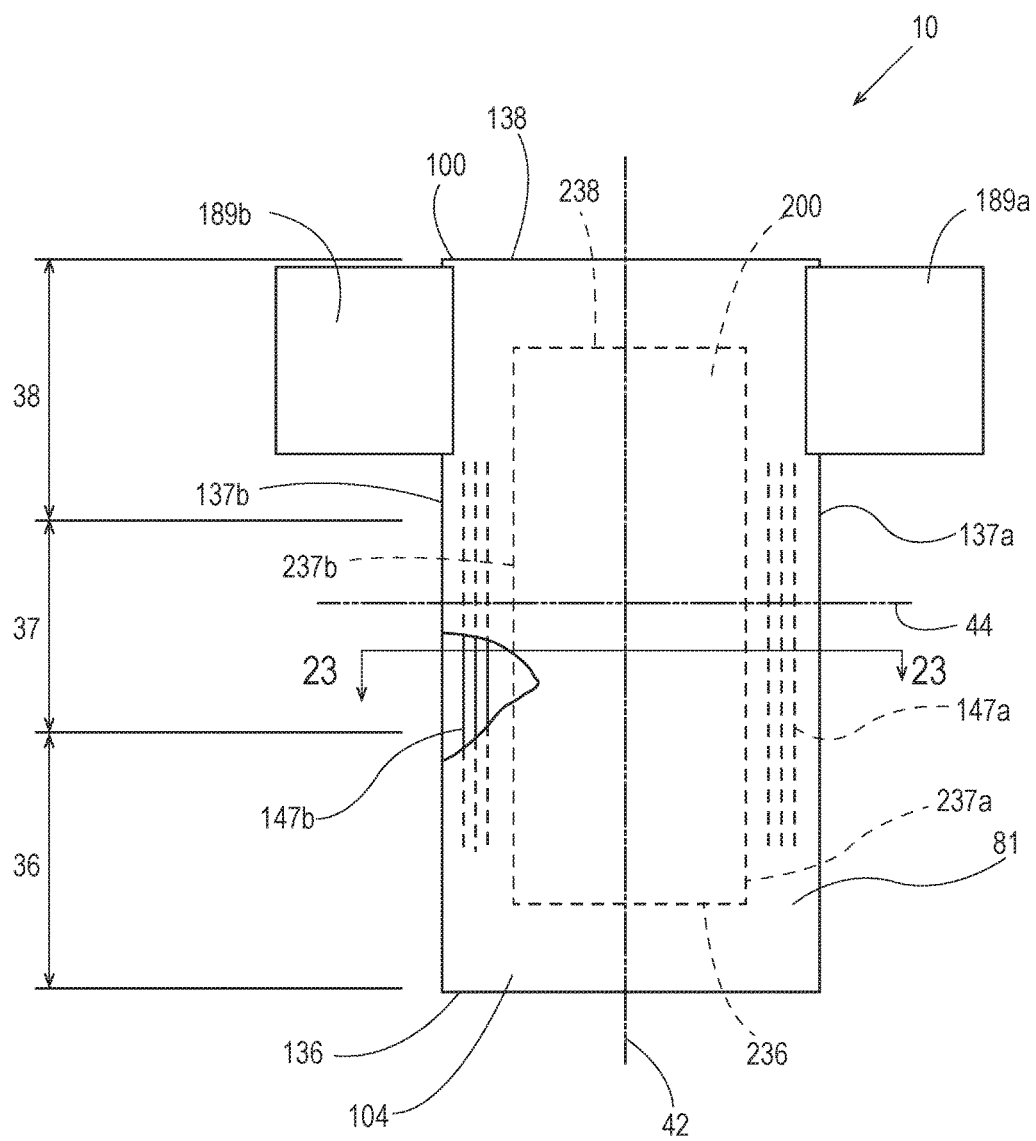
FIG. 18 is a partially cut away plan view of a pant diaper with a pair of flaps, wherein the wearer-facing interior of the diaper faces the viewer.
Figure 19:
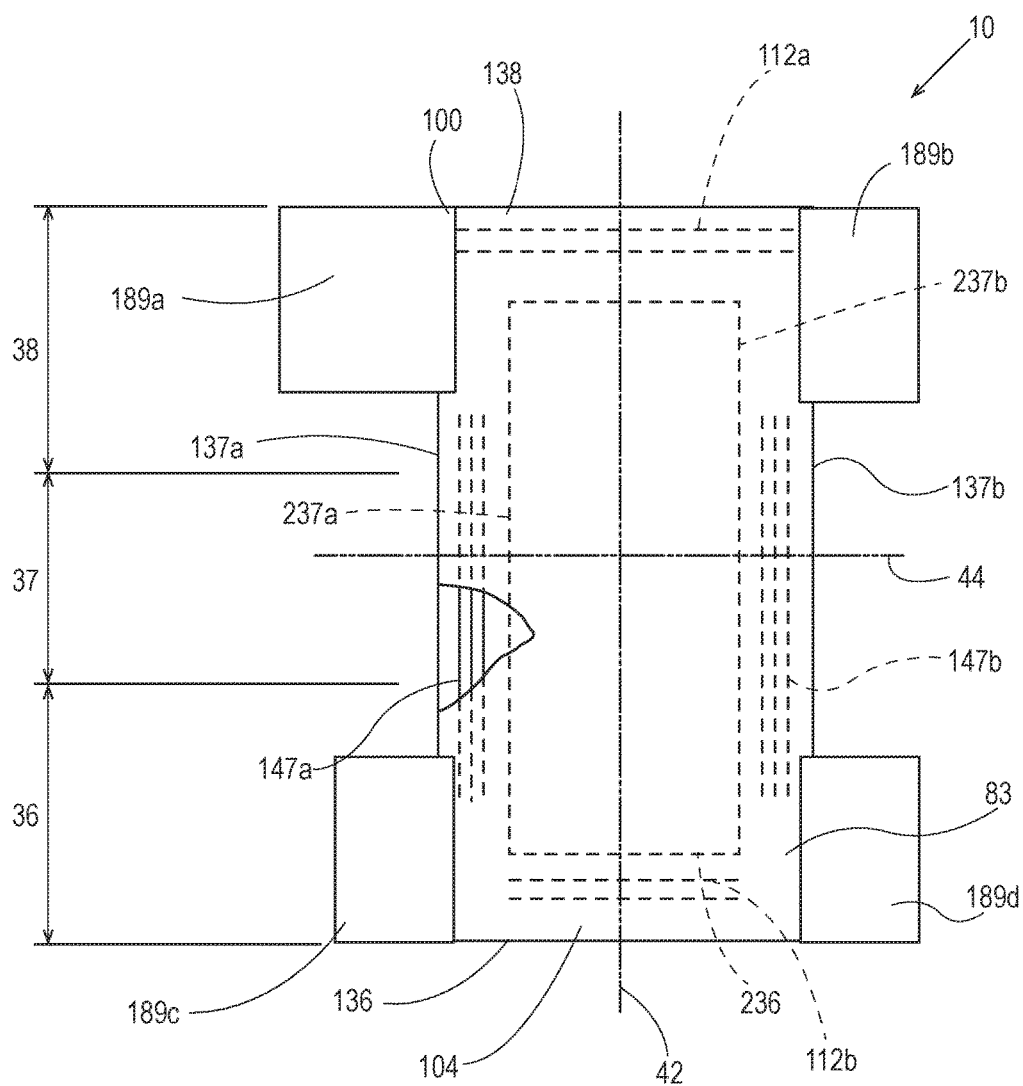
FIG. 19 is a partially cut away plan view a pant diaper with front and rear flaps, wherein the garment-facing exterior of the diaper faces the viewer.

In one embodiment, referring to FIGS. 18 and 19, the chassis 100 of the absorbent article 10 may comprise longitudinally extending and laterally opposing leg cuffs 147a and 147b that are disposed on the interior surface of the chassis 100 that faces inwardly toward the wearer and contacts the wearer. The leg cuffs 147a and 147b may comprise one or more elastic gathering members disposed at or adjacent the proximal edge of one or both of the leg cuffs 147. In addition, the elastic gathering members of the leg cuff may also comprise one or more elastic strands 146 disposed at or adjacent the distal edge of one or both of the leg cuffs 147. The elasticized leg cuffs 147 may comprise several embodiments for reducing the leakage of body exudates or fluids in the leg regions. The elasticized leg cuffs 147 are sometimes referred to as leg bands, barrier cuffs, elastic cuffs, or gasketing cuffs. Suitable elasticized leg cuffs 147 may comprise those described in U.S. Pat. Nos. 3,860,003, 4,909,803, 4,695,278, 4,795,454, 4,704,115, and 4,909,803, and U.S. Pat. Publ. No. 2009/0312730. The leg cuffs 147 may be formed by folding portions of the chassis 100 laterally inward, i.e., toward the longitudinal axis 42, to form both the respective leg cuffs 147 and the side edges 137a and b of the chassis 100. In other embodiments, the leg cuffs 147 may be formed by attaching an additional layer or layers to the chassis 100 at or adjacent to each of the respective side edges 137a and 137b of the chassis 100. In one embodiment, the chassis 100 may also comprise other elastics disposed adjacent the side edges 137 which may cause the article 10 to form into a "U" shape when allowed to relax thereby pulling the interior surface 102 of the front waist region 36 toward the interior surface 102 of the back waist region 38.

In one embodiment, each leg cuff 147 may comprise a proximal edge 157a and 157b. These edges 157a and 157b are positioned proximate to the longitudinal axis 42 compared to distal edges 139a and 139b. The leg cuffs 147 may overlap the absorbent core 200, i.e., the proximal edges 157a and 157b lie laterally inward of the respective side edges 237a and 237b of the absorbent core 200. Such an overlapped configuration may be desirable in order to impart a more finished appearance to the absorbent article 10 than that imparted by a non-overlapped configuration. In other embodiments, the leg cuffs 147 may not overlap the absorbent core 200.

In one embodiment, each leg cuff 147 may be attached to the interior surface 102 of the chassis 100 in a leg cuff attachment zone (not shown) adjacent to the front waist end edge 136 and in a longitudinally opposing leg cuff attachment zone (not shown) adjacent to the back waist end edge 138. In one embodiment, between the leg cuff attachment zones, the proximal edge 157 of the leg cuff 147 remains free, i.e., not attached to the interior surface 102 of the chassis 100 or to the absorbent core 200. Also, between the longitudinally opposing leg cuff attachment zones, each leg cuff 147 may comprise one or more (specifically including one, two, three, or four elastic strands per leg cuff 147) longitudinally extensible cuff elastic gathering members 159 that may be disposed at or adjacent to the proximal edge 157 of the leg cuff 147 by any suitable methods. Each of such cuff elastic gathering members 159 may be attached over the leg cuff's entire length or over only a portion of the leg cuff's length. For example, such cuff elastic gathering members 159 may be attached only at or near the leg cuff's longitudinally opposing ends and may be unattached at the middle of the leg cuff's length. Such cuff elastic gathering members 159 may be disposed in the crotch region 37 and may extend into one or both of the front waist region 36 and the back waist region 38. For example, an elastic gathering member 159 may be attached at or adjacent to the proximal edge 157 of each of the leg cuffs 147 and extends into both the front waist region 36 and the back waist region 38.

In various embodiments, each cuff elastic gathering member 159 may be enclosed inside a folded hem for example. In various embodiments, the cuff elastic gathering members 159 may be sandwiched between two layers forming the leg cuff 147, by two layers of the chassis 100, or may be attached on a surface of the chassis 100 or the leg cuff 147 and remain exposed.

In one embodiment, when stretched, the cuff elastic gathering member 159 disposed adjacent to each leg cuff's proximal edge 157 allows the leg cuff proximal edge 157 to extend to the flat uncontracted length of the chassis 100, e.g., the length of the chassis 100. When allowed to relax, the cuff elastic gathering member 159 contracts to pull the front waist region 36 and the back waist region 38 toward each other and, thereby, bend the article 10 into a "U" shape in which the interior of the "U" shape may be formed by the portions of the article 10 that are intended to be placed toward the body of the wearer (i.e., interior surface 102). Because each of the proximal edges 157 remains free between the longitudinally oriented leg cuff attachment zones, the contractive force of the elastic gathering member 159 may lift the proximal edge 157 of the leg cuff 147 away from the interior surface 102 of the chassis 100. This lifting of the proximal edges 157 when the article 10 is in the relaxed condition lifts the leg cuffs 147 into a position to serve as side barriers to prevent, or at least inhibit, leakage of bodily exudates.

Examples of acceptable leg cuffs 147 are disclosed in U.S. Ser. No. 13/457,521, filed Apr. 27, 2012, including the configurations disclosed by FIGS. 8a-t of the '521 application.

Waistband

In one embodiment, referring to FIG. 19, the article 10 may comprise an elasticized waistband 112a and b. The elasticized waistband may provide improved fit and containment and may be configured to elastically expand and contract laterally to dynamically fit a wearer's waist. The elasticized waistband may extend longitudinally from the waist edge of the absorbent article 10 toward the waist edge of the absorbent core 200. In one embodiment, the absorbent article 10 may have two elasticized waistbands, one positioned in the back waist region 38 and one positioned in the front waist region 36, although other pant embodiments may be constructed with a single elasticized waistband. The elasticized waistband may be constructed in a number of different configurations including those described in U.S. Pat. Nos. 4,515,595 and 5,151,092.

In one embodiment, the elasticized waistbands may comprise materials that have been "prestrained" or "mechanically prestrained" (i.e., subjected to some degree of localized pattern mechanical stretching to permanently elongate the material). The materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189, 3,025,199, 4,107,364, 4,209,563, 4,834, 741, and 5,151,092.

Flaps

The flaps 189 (a-d) may be discrete from or integral with the chassis 100. A discrete flap is formed as separate element, which is joined to the chassis 100. In some embodiments, this includes a plurality of flaps, e.g. 2 or 4 (often referred to as ear panels or side flaps) being joined to the side edges 137 a and b of the chassis in the front and/or rear waist regions 36 and 38 (see FIGS. 1 and 18-22). In other embodiments this may include a front and/or back belt-like flaps ("belts") being joined across the front and back (or rear) waist regions of the chassis 100, at least across end edges of the chassis 136 and 138 (see FIGS. 1 and 24). In some embodiments the waistbands 112 can overlap the flaps to create a continuous belt-like structure (see FIG. 19).

The belt-like flaps and may comprise an inner nonwoven layer and an outer nonwoven layer and elastics there between. The inner and outer nonwoven layers may be joined using adhesive or thermoplastic bonds. Various suitable belt-like flap configurations can be found in U.S. Pub. No. 2013-0211363.

An integral flap is a portion, one or more layers, of the chassis that projects laterally outward from the longitudinal edge. The integral flap may be formed by cutting the chassis to include the shape of the flap projection.

While many of the embodiments illustrated in this application having belt-like flaps are pant articles, taped articles may have belt-like flaps disposed in one or both waist regions as well.

The structure of flaps play an important role in the functionality of the absorbent article and are fundamentally different than the elastics used in underwear. As mentioned above, incontinence events, such as SUI and UUI, can result in a high flow rate and/or a full bladder release. The amounts of urine expelled during the incontinence events can vary wildly given the type of urinary incontinence as well as other circumstances such as time since last bathroom visit, amount of fluid intake, day or night, etc. Loadings can range from as low as a few drops of urine to loadings as high as 600 mls. It is not unusual to have single loadings as high as 300, 400 and even 500 mls. These levels of loading present a significant downward force associated with the loading which can be a pound or more. This downward force must be compensated for by the absorbent article chassis in order to minimize sagging, gapping and leakage. In order to sustain the fit of the article even after loading the article comprises elastomeric element(s) 146, including films and/or strands) that are disposed proximate to and along the side seams 280a and b (see, for example, FIG. 20, where the elastomeric elements 146 terminate proximate to and along the length of the seams 280a and b) of the article and extend laterally from one side toward the other. These elastomeric element(s) should create a normal force against the body sufficient to anchor the article. The location of the elastomeric element(s), as well as the forces exerted by the elastomeric element(s) can be varied to ensure proper anchoring at the hips and along the body specifically across the front waist region and in the back waist region. One form of anchoring beneficial for sustaining the fit of a loaded article is disclosed in U.S. Pat. No. 5,358,500 Absorbent Articles Providing Sustained Dynamic Fit issued Oct. 25, 1994 to LaVon, et al. It should also be noted that regular underwear with elastic along the waist edge and leg edges would not typically provide sufficient support to sustain the fit of the underwear if a weight of 300-600 grams was applied to the crotch region of the underwear. This paragraph illustrates another fundamental reason why proper Body Rise/Length of the absorbent article is key to maintain contact and gasketing, as well as proper anchoring on the body to overcome the fit degrading forces associated with high loadings.

The seams 280a and b may each be from about 150 mm to about 200 mm, from about 160 mm to about 190 mm, or from about 170 mm to about 180 mm. The seams are the portions of the flap that overlap (i.e., the distance from the waist opening to the leg opening of the overlapped or abutted flaps).

Fastening System

The absorbent article may also include a fastening system. When fastened, the fastening system interconnects the front waist region 36 and the rear waist region 38 resulting in a waist circumference that may encircle the wearer during wear of the absorbent article 10. The fastened elements connecting the front and back waist regions form refastenable side seams. This may be accomplished by flaps 189 a and b in the back waist region interconnecting with flaps 189 c and d in the front waist region or by flaps in the back waist region interconnecting with the chassis 100 in the front waist region. The fastening system may comprises a fastener 53 a and b such as tape tabs, hook and loop fastening components, interlocking fasteners such as tabs & slots, buckles, buttons, snaps, and/or hermaphroditic fastening components, although any other known fastening means are generally acceptable. The fasteners may releasably engage with a landing zone 118, which may be a woven or nonwoven. Some exemplary surface fastening systems are disclosed in U.S. Pat. Nos. 3,848,594; 4,662,875; 4,846,815; 4,894,060; 4,946,527; 5,151,092; 5,221,274. Particularly, the flaps may be configured as described and illustrated in FIGS. 3A-C and 4A-k of U.S. Ser. No. 61/666,065, filed on Jun. 29, 2012, titled DISPOSABLE ABSORBENT REFASTENABLE PANTS AND METHODS FOR MANUFACTURING THE SAME. Further, the absorbent articles of this disclosure may be manufactured in accordance with the descriptions and illustrations of U.S. Ser. No. 61/666,065 (see, for example, FIG. 5-10C of the '065 application). An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may be constructed to reduce shifting of overlapped portions or to improve fit as disclosed in U.S. Pat. Nos. 5,242,436; 5,499,978; 5,507,736; and 5,591,152.

Identical or Substantially Identical Chassis

As disclosed in U.S. Pub. No. 2013-0211355, it may be desirable to offer an array of packages for fitting different sized wearers, but comprising identical or substantially identical chassis. For instance, an array may comprise a first package comprising a first size of absorbent articles and a second package may comprise a second size of absorbent articles, where the first and second packages comprise identical or substantially identical chassis as described in U.S. Pub. No. 2013-0211355. More particularly, the first package may comprise a first chassis and the second package may comprise a second chassis, where each of the first and second chassis comprise the same dimensions of one or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width.

Further, each of the first and second chassis may comprise identical chemical compositions of one or more of a topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

And, each of the first and second chassis may comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

And, each of the first and second chassis may comprise compositionally identical core super absorbent polymers. The first and second chassis may have identical component cross sectional order and disposition in at least one of the front waist region, back waist region, and crotch region. The inner leg cuffs of the first and second chassis may be composed of the compositionally identical materials.

And, the core adhesives of the first and second chassis may be the same adhesive(s). The first and second chassis may comprise core super absorbent polymers that are in the same chemical class and subclass.

And, each of the first and second chassis may comprise first and second wetness indicators, respectively, and wherein the first and second wetness indicators are compositionally identical.

Further, the inner leg cuffs of the first and second chassis may have identical component cross sectional order and disposition in at least one of the front waist region, back waist region, and crotch region. The distance from the left outer cuff distal edge to a right outer cuff distal edge may the same. The distance from the left inner cuff proximal edge to left outer cuff distal edge may be the same. The distance from the left inner cuff proximal edge to the right inner cuff proximal edge is the same. The lengths of the inner and outer cuffs are the same.

In some embodiments, different size offerings in an array may have identical or substantially identical chassis as the flaps or belts may be used to enable the absorbent article to fit different sized wearers. For example, first and second absorbent articles may have identical chassis (compositionally, dimensionally, cross-sectionally), but the first article may have a different length due to disposition of the belts, such that the first article may be targeted to fit a smaller wearer than the second article. As a second example, first and second absorbent articles may have identical chassis (compositionally, dimensionally, cross-sectionally), but the first article may have a different length and/or width due to the size of the belts, such that the first article may be targeted to fit a smaller wearer than the second article.

In some embodiments, first and second absorbent articles may have identical chassis compositionally, but not dimensionally, and not cross-sectionally. In some embodiments, first and second absorbent articles may have identical chassis dimensionally, but not compositionally, and not cross-sectionally. In some embodiments, first and second absorbent articles may have identical chassis cross-sectionally, but not dimensionally, and not compositionally. In still other embodiments, first and second absorbent articles may have two, but not three of (1) compositionally, (2) dimensionally, and (3) cross-sectionally identical chassis.

What is claimed is:

1. An array of packages comprising two or more different sizes of disposable absorbent articles, the array comprising:
   a first package comprising a first disposable absorbent article, the first disposable absorbent article comprising a first topsheet, a first backsheet, a first absorbent core comprising first and second channels, and a first pair of side seams, the first absorbent article being a first size and in closed form;
   a second package comprising a second disposable absorbent article, the second disposable absorbent article comprising a second topsheet, a second backsheet, a second absorbent core comprising third and fourth channels, and a second pair of side seams, the second absorbent article being a second size and in closed form;
   wherein the second size is larger than the first size;
   wherein a Channel Spacing of the first size is greater than a Channel Spacing of the second size; and
   wherein the first package and the second package are in the same array.

2. The array of packages of claim 1, wherein a Channel Curvature of the first size is equal to or greater than a Channel Curvature of the second size.

3. The array of packages of claim 1, wherein a Channel Arm Angle of the first core is equal to or greater than a Channel Arm Angle of a second core.

4. The array of packages of claim 1, wherein a Channel Length of the first core is equal to or greater than a Channel Length of the second core.

5. The array of packages of claim 1, wherein the Channel Spacing of the third and fourth channels of the second absorbent core is from about 10 mm to about 50 mm.

6. The array of packages of claim 1, wherein the Channel Spacing of the first and second channels of the first absorbent core is from about 30 mm to about 80 mm.

7. The array of packages of claim 1, wherein a Channel Curvature of a first channel of the first absorbent core is greater than a Channel Curvature of a third channel of the second absorbent core.

8. The array of packages of claim 1, wherein a Channel Curvature of the third channels of the second absorbent core is from about 5/m to about 11 m.

9. The array of packages of claim 1, wherein a Channel Curvature of the first channel of the first absorbent core is from about 7/m to about 15/m.

10. The array of packages of claim 1, wherein a Channel Arm Angle of the firs channel of the first absorbent core is greater than a Channel Arm Angle of the third channel of the second absorbent core.

11. The array of packages of claim 10, wherein the Channel Arm Angle of the third channel of the second absorbent core is from about 5° to about 23°.

12. The array of packages of claim 10, wherein the Channel Arm Angle of the first channel of the first absorbent core is from about 18° to about 30°.

13. The array of packages of claim 1, wherein a Channel Length of the third channel of the second absorbent core is greater than a Channel Length of the first channel of the first absorbent core.

14. The array of packages of claim 13, wherein the Channel Length of the first channel of the first absorbent core is from about 200 mm to about 350 mm.

15. The array of packages of claim 13, wherein the Channel Length of the third channel of the second absorbent core is from about 250 mm to about 400 mm.

16. The array of packages of claim 1, wherein at least one of the first and third channels are substantially free from airfelt and super absorbent polymer.

17. The array of packages of claim 1, wherein at least one of the first and third channels comprise a substantially linear segment.

18. The array of packages of claim 1, wherein the array comprises a third package comprising a third absorbent article comprising a third absorbent core comprising fifth and sixth channels, the third absorbent article being a third size, wherein a Channel Spacing of the third size is equal to or greater than Channel Spacing of the second size.

19. The array of packages of claim 1, wherein the array comprises a third package comprising a third absorbent article comprising a third absorbent core comprising fifth and sixth channels, the third absorbent article being a third size, wherein a Channel Curvature of the second size is greater than a Channel Curvature of the third size.

20. The array of packages of claim 1, wherein the array comprises a third package comprising a third absorbent article comprising a third absorbent core comprising fifth and sixth channels, the third absorbent article being a third size, wherein a Channel Length of the second size is less than a Channel Length of the third size.

* * * * *